United States Patent
Park et al.

(10) Patent No.: US 11,127,272 B2
(45) Date of Patent: Sep. 21, 2021

(54) ELECTRONIC GAS SENSORS AND METHOD FOR CONTROLLING GAS SENSORS

(71) Applicant: SAMSUNG ELECTRONICS CO., LTD., Suwon-si (KR)

(72) Inventors: Jang-pyo Park, Hwaseong-si (KR);
Sang-hun Lee, Yongin-si (KR);
Yong-won Jeong, Seoul (KR);
Jeong-eun Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 204 days.

(21) Appl. No.: 16/464,575

(22) PCT Filed: Dec. 11, 2017

(86) PCT No.: PCT/KR2017/014444
§ 371 (c)(1),
(2) Date: May 28, 2019

(87) PCT Pub. No.: WO2018/106082
PCT Pub. Date: Jun. 14, 2018

(65) Prior Publication Data
US 2021/0104140 A1   Apr. 8, 2021

(30) Foreign Application Priority Data

Dec. 9, 2016   (KR) .................. 10-2016-0167831
Nov. 9, 2017   (KR) .................. 10-2017-0148933

(51) Int. Cl.
G08B 17/117    (2006.01)
G05B 15/02     (2006.01)
F24F 11/88     (2018.01)

(52) U.S. Cl.
CPC ............ *G08B 17/117* (2013.01); *F24F 11/88* (2018.01); *G05B 15/02* (2013.01)

(58) Field of Classification Search
CPC ......... G08B 17/117; G05B 15/02; F24F 11/88
See application file for complete search history.

(56) References Cited

U.S. PATENT DOCUMENTS 4,542,640 A * 9/1985 Clifford ............ G01N 33/0031
422/98
4,638,443 A * 1/1987 Kaneyasu ............ G08B 17/117
340/634

(Continued)

FOREIGN PATENT DOCUMENTS

EP   3101422 A1   12/2016
JP   4-39029 B2    6/1992

(Continued)

OTHER PUBLICATIONS

International Search Report (PCT/ISA/210) dated Mar. 19, 2018, issued by the International Searching Authority in International Application No. PCT/KR2017/014444.

(Continued)

*Primary Examiner* — Ramesh B Patel
(74) *Attorney, Agent, or Firm* — Sughrue Mion, PLLC

(57) ABSTRACT

An electronic apparatus is provided. The electronic apparatus according to an embodiment includes a plurality of different types of gas sensors configured to output sensing values based on sensing a gas, and a processor configured to determine a gas type corresponding to a plurality of sensing values respectively output from the plurality of different types of gas sensors.

15 Claims, 23 Drawing Sheets

(56) References Cited

U.S. PATENT DOCUMENTS

| | | | |
|---|---|---|---|
| 5,987,964 A | 11/1999 | Miremadi | |
| 6,235,243 B1* | 5/2001 | Fleischer | G01N 27/12 422/94 |
| 6,960,476 B2* | 11/2005 | Morris | G01N 33/0031 422/50 |
| 6,975,944 B1 | 12/2005 | Zenhausern | |
| 7,302,313 B2 | 11/2007 | Sharp et al. | |
| 7,460,958 B2* | 12/2008 | Walsh | G01N 33/0034 702/24 |
| 8,186,201 B2 | 5/2012 | Petrovic | |
| 8,988,232 B1 | 3/2015 | Sloo et al. | |
| 9,332,322 B2 | 5/2016 | Niemeyer et al. | |
| 10,386,351 B2* | 8/2019 | Savoy | G01N 33/0036 |
| 2008/0302672 A1 | 12/2008 | Sandvik et al. | |
| 2014/0060012 A1* | 3/2014 | Kakimoto | F01N 11/007 60/277 |
| 2014/0260529 A1* | 9/2014 | Pruente | G01N 33/2841 73/19.11 |
| 2015/0136376 A1 | 5/2015 | Niemann et al. | |
| 2015/0204753 A1* | 7/2015 | Scheucher | G01M 3/26 700/275 |
| 2016/0121255 A1 | 5/2016 | Zhang et al. | |
| 2016/0123622 A1 | 5/2016 | Fu et al. | |
| 2016/0187279 A1 | 6/2016 | Tayebi et al. | |
| 2016/0202225 A1* | 7/2016 | Feng | G01N 33/0032 436/141 |
| 2016/0334320 A1* | 11/2016 | Cho | H04N 5/2256 |
| 2016/0356764 A1 | 12/2016 | Martin et al. | |
| 2017/0115248 A1* | 4/2017 | Lin | G01N 27/127 |
| 2017/0160221 A1* | 6/2017 | Savoy | G01N 33/0008 |
| 2017/0167999 A1* | 6/2017 | Akasaka | B81B 7/0061 |
| 2018/0024091 A1* | 1/2018 | Wang | H04B 1/713 204/431 |
| 2018/0112583 A1* | 4/2018 | Okamoto | G01N 27/419 |
| 2018/0120278 A1* | 5/2018 | Hoorfar | G01N 33/497 |
| 2018/0138859 A1* | 5/2018 | Shin | H03B 5/364 |
| 2018/0202960 A1* | 7/2018 | Ono | G01N 27/28 |
| 2018/0372618 A1* | 12/2018 | Kwak | G01N 21/03 |

FOREIGN PATENT DOCUMENTS

| | | |
|---|---|---|
| JP | 7-234198 A | 9/1995 |
| JP | 11-264809 A | 9/1999 |
| JP | 2006-21145 A | 1/2006 |
| JP | 2012-112651 A | 6/2012 |
| KR | 10-2008-0028157 A | 3/2008 |
| KR | 10-1307189 B1 | 9/2013 |
| KR | 10-2016-0001369 A | 1/2016 |

OTHER PUBLICATIONS

Written Opinion (PCT/ISA/237) dated Mar. 19, 2018, issued by the International Searching Authority in International Application No. PCT/KR2017/014444.

Communication dated Nov. 18, 2019, issued by the European Patent Office in counterpart European Application No. 17878464.1.

* cited by examiner

Acetone  Benzene

2————————1  2————————1

Cyclohexane  Ethanol

2————————1

Methanol

Acetone

Benzene

Cyclohexane

Ethanol

Methanol

Acetone

Benzene

Cyclohexane

Ethanol

Methanol

Acetone

Benzene

Cyclohexane

Ethanol

Methanol

ELECTRONIC GAS SENSORS AND METHOD FOR CONTROLLING GAS SENSORS

TECHNICAL FIELD

Devices and methods consistent with what is disclosed herein relate to an electronic apparatus and a controlling thereof, and more particularly, to an electronic apparatus for determining a gas type using a plurality of gas sensors and a controlling method thereof.

BACKGROUND ART

A gas sensor is a device for measuring the concentration of a specific gas, and provided in an apparatus, for example, an air conditioner to measure contaminants such as volatile organic compounds (VOC), or the like.

The types of gas sensors may include a semiconductor type gas sensor, a contact combustion type sensor, an electrochemical type sensor, and the like in accordance with the measurement principle. Among them, the semiconductor type gas sensor measures the amount of gas by using the degree of change of the resistance value as the material to be measured, which is adsorbed on the surface is oxidized or reduced.

However, since most of the gases except the inert gas tend to be oxidized/reduced, in the semiconductor type gas sensor, not only the target gas to be measured but also other gases existing together therewith are also sensed. Therefore, there is a problem that it is not possible to distinguish what type of gas is contained in the sensed gas, but only the concentration of the gas can be measured through the gas sensor.

CONTENT OF THE INVENTION

Task to be Resolved

An aspect of the exemplary embodiments relates to providing an electronic apparatus for determining a gas type using a plurality of gas sensors and a method for controlling the same.

Means for Resolving the Task

According to an exemplary embodiment, there is provided an electronic apparatus including a plurality of different types of gas sensors configured to output sensing values based on sensing a gas, and a processor configured to determine a gas type corresponding to a plurality of sensing values respectively output from the plurality of different types of gas sensors.

The electronic apparatus may further include a storage configured to store a plurality of pieces of reference information respectively corresponding to a plurality of different types of gases, wherein each of the plurality of pieces of reference information is a piece of information on a ratio between the plurality of sensing values output from the plurality of gas sensors corresponding to sensing a same gas, and wherein the processor is further configured to detect reference information corresponding to the plurality of output sensing values among the plurality of pieces of stored reference information, and determine that a gas type corresponding to the detected reference information is a type of the sensed gas.

The plurality of gas sensors each may include a semiconductor layer that reacts with a gas.

Semi-conductor layers of the plurality of gas sensors may be different in at least one of constituent materials, ratios, and thicknesses of the constituent materials.

The processor may measure a concentration of the sensed gas based on a magnitude of at least one of the plurality of output sensing values.

The processor may estimate a concentration of carbon dioxide in accordance with the measured concentration based on the sensed gas being volatile organic compound (VOC).

The electronic apparatus may further include a filter configured to filter air, and a fan configured to provide outside air to the filter, wherein the processor controls a rotational speed of the fan according to the determined gas type.

The processor may be further configured to control the fan not to rotate, or to rotate at a predetermined speed based on the determined gas type not being harmful to a human body, and control the fan to rotate at a higher speed than the predetermined speed based on the determined gas type being harmful to a human body.

The electronic apparatus may further include a communicator configured to communicate with the other electronic apparatus, wherein the processor controls the communicator to transmit a control command corresponding to the determined gas type to at least one of a display device, a danger alarming device, a window automatic opening and closing device, and a ventilation device.

The processor may control the communicator to transmit a control command to allow a UI screen including information on the determined gas type to be displayed on the display device.

The electronic apparatus may further include at least one of a temperature sensor, a humidity sensor, and a dust sensor.

The plurality of gas sensors and the processor may be embodied as a single chip.

According to an exemplary embodiment, there is provided a method for controlling an electronic apparatus including a plurality of different types of gas sensors, the method including outputting a sensing value by each of the plurality of different types of gas sensors based on sensing a gas, and determining a gas type corresponding to a plurality of sensing values respectively output from the plurality of different types of gas sensors.

The electronic apparatus may store a plurality of pieces of reference information respectively corresponding to a plurality of different types of gases, wherein each of the plurality of pieces of reference information is a piece of information on a ratio between the plurality of sensing values output from the plurality of gas sensors corresponding to sensing a same gas, and wherein the determining comprises detecting reference information corresponding to the plurality of output sensing values among the plurality of pieces of stored reference information, and determining that a gas type corresponding to the detected reference information is a type of the sensed gas.

The method may further include measuring a concentration of the sensed gas based on a magnitude of at least one of the plurality of output sensing values.

The method may further include estimating a concentration of carbon dioxide based on the measured concentration based on the sensed gas being volatile organic compound (VOC).

The electronic apparatus may further include a filter for filtering air and a fan for providing outside air to the filter, and the method for controlling the electronic apparatus may further include controlling a rotational speed of the fan according to the determined gas type.

The controlling may include controlling the fan not to rotate, or to rotate at a predetermined speed based on the determined gas type not being harmful to a human body, and controlling the fan to rotate at a higher speed than the predetermined speed based on the determined gas type being harmful to a human body.

The method may further include transmitting a control command corresponding to the determined gas type to at least one of a display device, a danger alarming device, a window automatic opening and closing device, and a ventilation device.

According to an exemplary embodiment, there is provided a computer readable recording medium including a program for executing a controlling method of an electronic apparatus including a plurality of different types of gas sensors, the method comprising outputting a sensing value by each of the plurality of gas sensors based on sensing a gas, determining a gas type corresponding to the plurality of sensing values respectively output from the plurality of gas sensors as a type of the sensed gas.

BRIEF DESCRIPTION OF THE DRAWINGS

FIG. 2A to FIG. 2D are diagrams illustrating sensing values of a plurality of semi-conductor gas sensors of different types;

DETAILED CONTENT FOR IMPLEMENTING THE INVENTION

Figure 1:
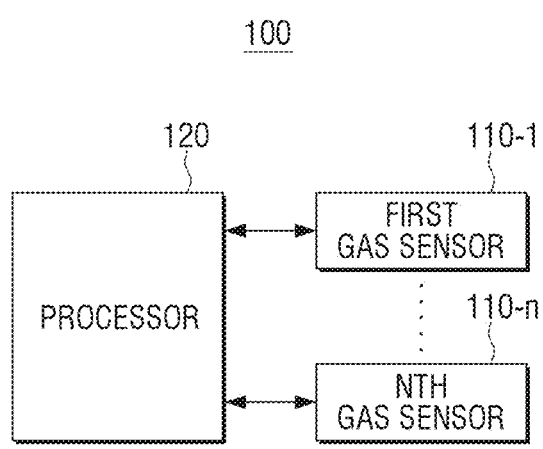
FIG. 1 is a block diagram to explain a configuration of an electronic apparatus according to an embodiment.

In describing exemplary embodiments, detailed description of relevant known functions or components may be omitted if it would obscure the description of the subject matter. The terms used below are defined in consideration of the functions of the disclosure, and this may vary depending on the intention or the relationship of the user, the operator, or the like. Therefore, the definition should be based on the contents throughout this specification.

The terms such as "first," "second," and so on may be used to describe a variety of elements, but the elements should not be limited by these terms. The terms are used simply to distinguish one element from other elements.

The terms used in this disclosure are used only to describe particular embodiments, and are not intended to limit the scope of claims. The singular expression also includes the plural meaning as long as it does not differently mean in the context. In this specification, terms such as 'include' and 'have/has' should be construed as designating that there are such characteristics, numbers, operations, elements, components or a combination thereof in the specification, not to exclude the existence or possibility of adding one or more of other characteristics, numbers, operations, elements, components or a combination thereof.

In an exemplary embodiment, 'a module', 'a unit', or 'a part' perform at least one function or operation, and may be realized as hardware, such as a processor or integrated circuit, software that is executed by a processor, or a combination thereof. In addition, a plurality of 'modules', a plurality of 'units', or a plurality of 'parts' may be integrated into at least one module or chip and may be realized as at least one processor except for 'modules', 'units' or 'parts' that should be realized in a specific hardware.

Hereinafter, embodiments of the disclosure will be described in detail with reference to the accompanying drawings so that those skilled in the art can easily carry out the invention. However, the disclosure may be embodied in many different forms and is not limited to the embodiments described herein. In order to clearly illustrate the disclosure in the drawings, some of the elements that are not essential to the complete understanding of the disclosure are omitted for clarity, and like reference numerals refer to like elements throughout the specification.

Hereinafter, the disclosure will be described in more detail with reference to the drawings.

FIG. 1 is a block diagram to explain a configuration of an electronic apparatus according to an embodiment.

Referring to FIG. 1, an electronic apparatus 100 may include a plurality of gas sensors 110-1 to 110-n, and a processor 120.

The electronic apparatus 100 may be embodied in various forms of apparatuses. For example, the electronic apparatus 100 may be implemented as home appliances such as an air purifier, a dehumidifier, an air conditioner, a refrigerator, a washing machine, a kimchi refrigerator, a cleaner, or the like, electronic products such as a smart phone, a tablet PC, or the like, or wearable devices such as a smart watch, a patch, a glove, a band, a necklace, a bracelet, a ring, a headband, an earphone, an earring, a clothing, or the like. It can also be implemented as a gas sensing device itself.

The plurality of gas sensors 110-1 to 110-n may output sensing values corresponding to the concentration of gas.

For example, the plurality of gas sensors 110-1 to 110-n may be semiconductor gas sensors, but any type of sensor can be used as long as it senses the concentration of gas in the air.

For example, the plurality of gas sensors 110-1 to 110-n could be total volatile organic compound (TVOC) sensors.

The disclosure can identify the type of gas using a plurality of gas sensors for sensing the concentration of gas. The plurality of gas sensors 110-1 to 110-n may be different types of gas sensors, and if they are different in type, it may mean that they have different methods of sensing a gas. For example, a gas sensing method may include a contact combustion method, an electrochemical method (e.g., a solution conduction method, a constant potential method, and a diaphragm electrode method), a thermal conductivity method, an optical method (e.g., an infrared absorption method, a visible absorption method, and an optical interference method), an electric method (e.g., a hydrogen ionization method, a thermal conduction method, a contact combustion method, and a semiconductor method), a reaction coloring method, a solution conductivity method, a solid electrolyte method, a gas chromatography method, or the like.

The semiconductor system may use a phenomenon in which the conductivity increases when a reducing gas is adsorbed to a semiconductor of a metal oxide (N-type). In the contact combustion system, when a combustible gas is burned by a catalyst such as platinum, and the temperature rises, the rise of the temperature may be determined as the rise of the electrical resistance of the platinum wire to measure the concentration of the reaction gas. In the electrochemical system, the centration of gas may be measured by providing an electrode in the electrolyte (e.g., Conc-$H_2SO_4$), applying a voltage between electrodes, oxidizing gas, and measuring the current. The thermal conductivity method may be a method of measuring the concentration of gas by measuring the resistance values of a platinum wire and a thermistor by using a thermal conductivity determined by gas nearby. The optical interference method may be a method of measuring the concentration of gas by using an interference pattern due to a difference in refractive index between air and object. The reaction coloring method may be a method for measuring the concentration of gas by reacting gas to a liquid or a solid to develop color and measuring the degree of coloring optically. The solution conductivity method may be a method for measuring the concentration of gas by absorbing gas to be measured into an appropriate solution and measuring the change in the conductivity of the solution. The solid electrolyte method is a method for measuring the concentration of gas by using the electromotive force generated by the partial pressure difference when a difference in oxygen partial pressure between both sides occurs through the solid electrolyte having oxygen ion conductivity.

For another example, if the plurality of gas sensors 110-1 to 110-n are different in type, it may mean that the method of sensing gas is the same (e.g., the plurality of gas sensors 110-1 to 110-n use the thermal conductivity method in the same manner), but the process of manufacturing a gas sensor is different. If the process of manufacturing a gas sensor is different, it may mean the sensor shape is different, a constituent element of the sensor is different, the manufacturer of the sensor is different, or the manufacturing date, version, etc. are different although the manufacturer of the sensor is the same. Although the sensors sense the gas in the same manner, but with different manufacturing processes, different sensing results may be output despite having the same environment. Therefore, the disclosure may adopt such feature.

It is assumed that the plurality of gas sensors 110-1 to 110-n are semi-conductor gas sensors. However, the disclosure is not limited thereto, but any type of sensor may be used as long as it can measure the concentration of gas.

The semi-conductor gas sensor may be a sensor that uses the characteristic that the electric conductivity changes depending on the type of gas or semi-conductor when gas is applied to the high-temperature sensor. According to an embodiment, various types of semi-conductor gas sensors may be used.

For example, the semiconductor gas sensor may be classified into a bulk type, a thick film type, a thin film type, and the like depending on the sensor attachment structure, a cylindrical type, a thick film type, a disk type, and the like depending on the shape, and a ceramic gas sensor, an integrated ultrafine particle gas sensor, a CFT gas sensor, a MOSFET type, a diode type, and the like depending on the constitution. The semiconductor gas sensor may include a semiconductor layer that reacts with the gas, a heater that heats the semiconductor layer to an appropriate temperature, and an electrode that transmits the electrical conductivity change in the semiconductor layer to the outside as an electrical signal. The concentration of gas may be determined using the resistance change according to the reaction in the semi-conductor layer.

The electrode of the semiconductor gas sensor may vary depending on the structure, size, and material of the electrode. As the electrode material, for example, tungsten, silver, platinum, gold or the like may be used. The type of electrode may be a measurement electrode, a heater electrode, and the like, and the shape of electrode may be, for example, a transparent electrode.

The heater of the semiconductor gas sensor may be, for example, a platinum heater, a graphene heater (transparent), a chemical material coating type, or the like. The heater voltage may be adjusted by the type of electrode included in the semiconductor gas sensor, the semiconductor layer constituent material, the type of gas to be measured, etc. For example, the heater voltage may be set to 5V, and the heater current may be set to 160 mA, or the heater voltage may be set to 2.5V, and the heater current may be set to 200 mA.

Meanwhile, in this specification, the sensing value described as being output from the semiconductor gas sensor may include at least one of various information such as a resistance value, a current value, a relative change amount, a resistance value by a semiconductor layer component, a resistance value change by a heater voltage and a heater current, or the like.

Different types of semiconductor gas sensors may be manufactured by changing the properties of the semiconductor layers included in the semiconductor gas sensor. Elements that can change the properties of the semiconductor layer may include the constituent components, the ratio or the thickness of the constituent components, and the like.

Examples of materials that constitute the semiconductor layer included in the semiconductor gas sensor may include $SnO_2$, $ZnO$, $WO_3$, $TiO_2$, $In_2O_3$, $Pd$, $Fe_2O_3$, $ThO_2$, $AlN$, $ZrO_2$, $CoO$, $LaAlO_3$, $Co_3O_4$, $NiO$, $CuO$, etc. Each of the semiconductor layers included in the plurality of gas sensors 110-1 to 110-n may include any one or two or more of the above-described materials, and each semiconductor layer may be different in at least one of the constituent components, the ratio or the thickness of the constituent components, and the like. For example, the semiconductor layer of the first gas sensor 110-1 among the plurality of gas sensors 110-1 to 110-*n* may be composed in a ratio (in units of %) of SnO2, PdCl2, and NGO of 98:1:1, and the semiconductor layer of the second gas sensor 110-2 may be composed in a ratio of (in units of %) of TiO2 and ZnO of 98:2.

The plurality of gas sensors 110-1 to 110-*n* having semiconductor layers with different properties may react to the same gas differently. Therefore, different sensing values may be output even in the same environment. The some examples in this regard will be illustrated in FIG. 2A to FIG. 2D.

Although the constituent element, the type of constituent element, the ratio and thickness of the constituent element, etc. are the same, the sensitivity (%) may be different due to the difference in the uniformity, temperature or the humidity of the constituent elements. Therefore, when the measured sensitivity (e.g., a resistance change rate, a current change rate, etc.) is equal to or less than a predetermined threshold value, the measured sensitivity may be changed to a predetermined value, and a sensing value may be output based on the changed sensitivity.

FIG. 2A to FIG. 2D are diagrams illustrating sensing values of a plurality of semi-conductor gas sensors of different types with respect to acetone, benzene, cyclohexane, ethanol, and methanol.

FIG. 2A is a view illustrating an example using two semiconductor gas sensors in different types. Referring to FIG. 2A, each of two lines extending outwardly from the center corresponds to two semiconductor gas sensors in different types, and a sensing value of each semi-conductor gas sensor is shown in bold on each line. It can be known that the ratio between sensing values of two semiconductor gas sensors may vary depending on the gas type.

Figure 2B:
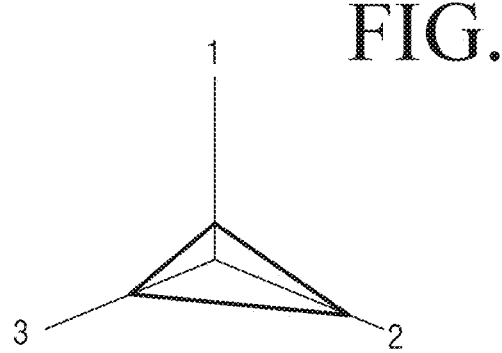
Figure 2B:
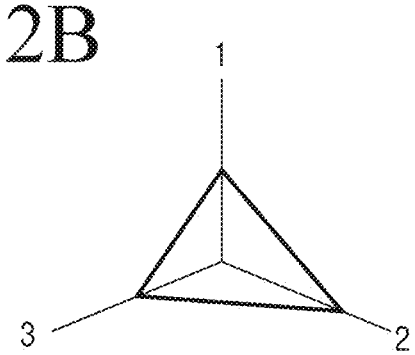
Figure 2B:
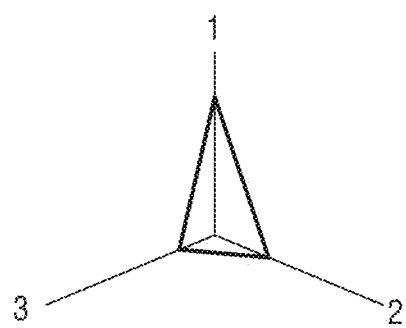
Figure 2B:
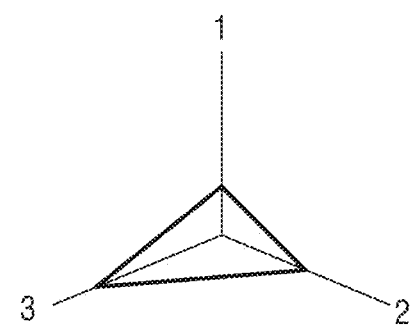
Figure 2B:
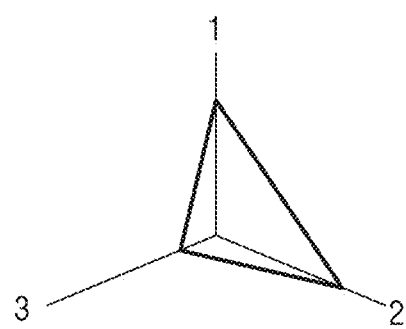

FIG. 2B is a view illustrating an example using three different type semiconductor gas sensors. Referring to FIG. 2B, three lines extending outwardly from the center of the circular diagram correspond to three different types of semiconductor gas sensors, respectively. The sensing value of each semiconductor sensor is shown on each line, and the lines are connected to one another in bold. It can be known that the ratio between the sensing values of three semiconductor gas sensors may vary depending on the gas type.

Figure 2C:
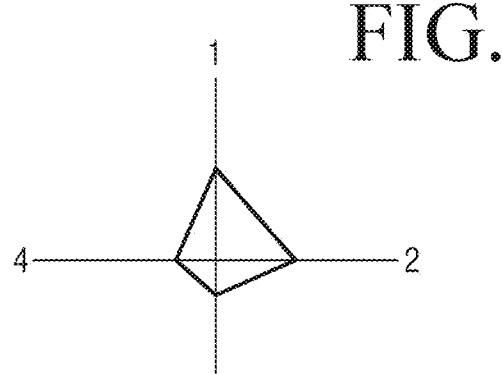
Figure 2C:
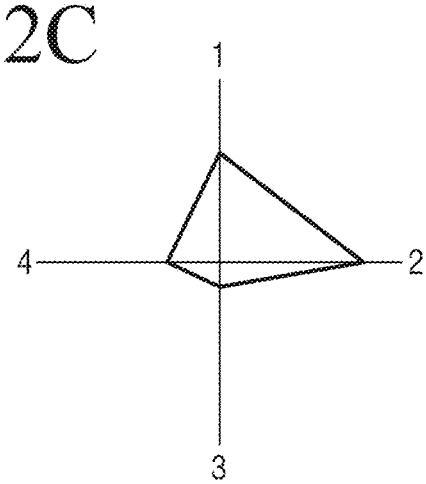
Figure 2C:
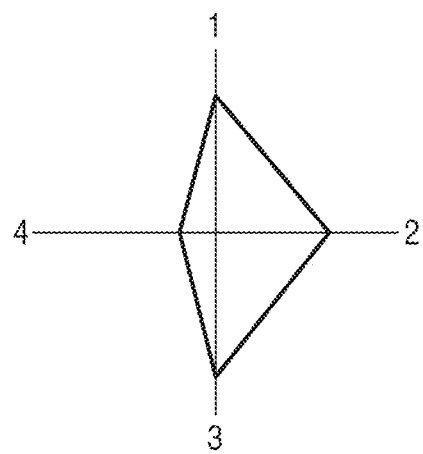
Figure 2C:
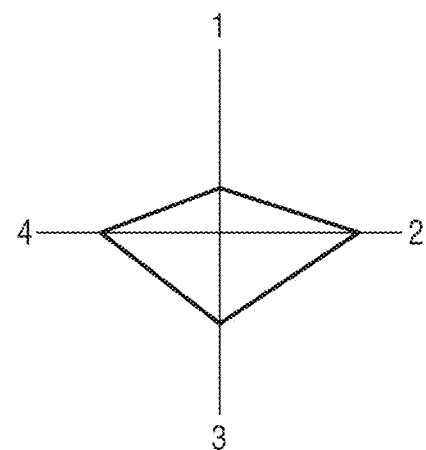
Figure 2C:
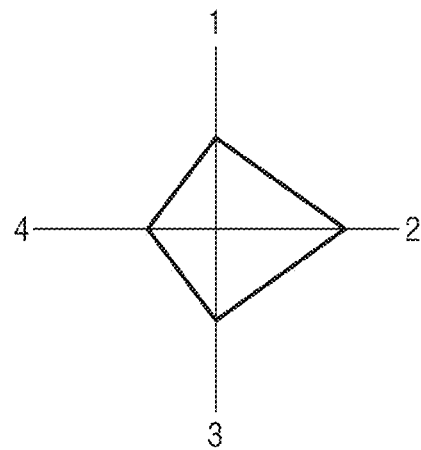
Figure 2D:
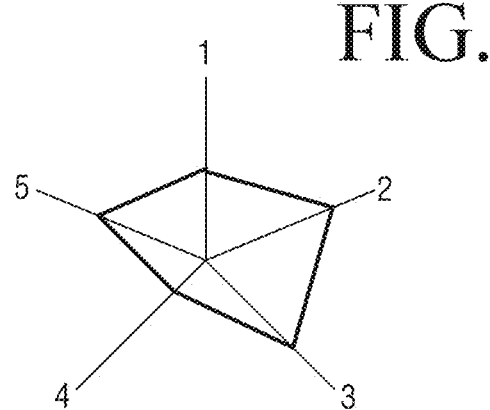
Figure 2D:
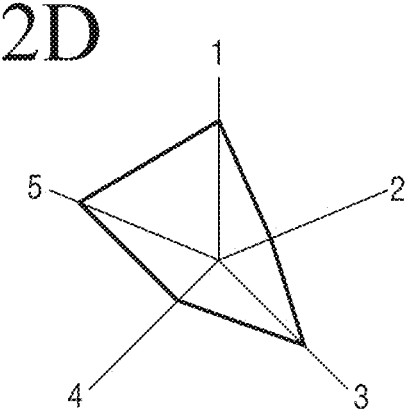
Figure 2D:
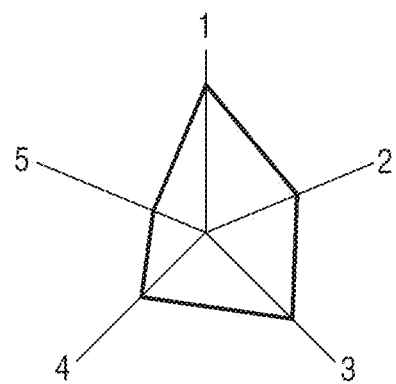
Figure 2D:
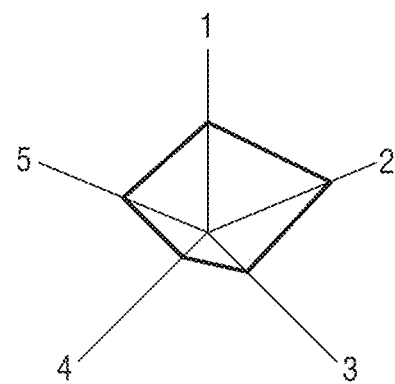
Figure 2D:
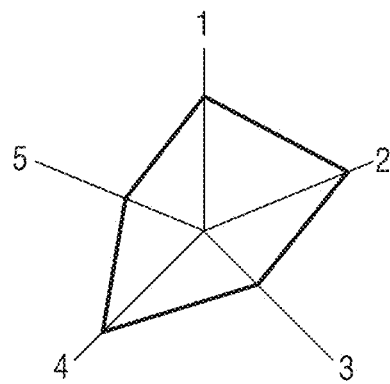

FIG. 2C is a view illustrating four different types of semiconductor gas sensors, and FIG. 2D is a view illustrating five different types of semiconductor gas sensors.

The plurality of sensing values output from the plurality of gas sensors each may have a unique pattern for each gas type. According to an embodiment, the type of gas may be determined based thereon.

FIG. 2A to FIG. 2D describe that two to five gas sensors are used, but it is not limited thereto. Six or more of gas sensors may constitute the electronic apparatus 100 according to an embodiment.

Figure 3:
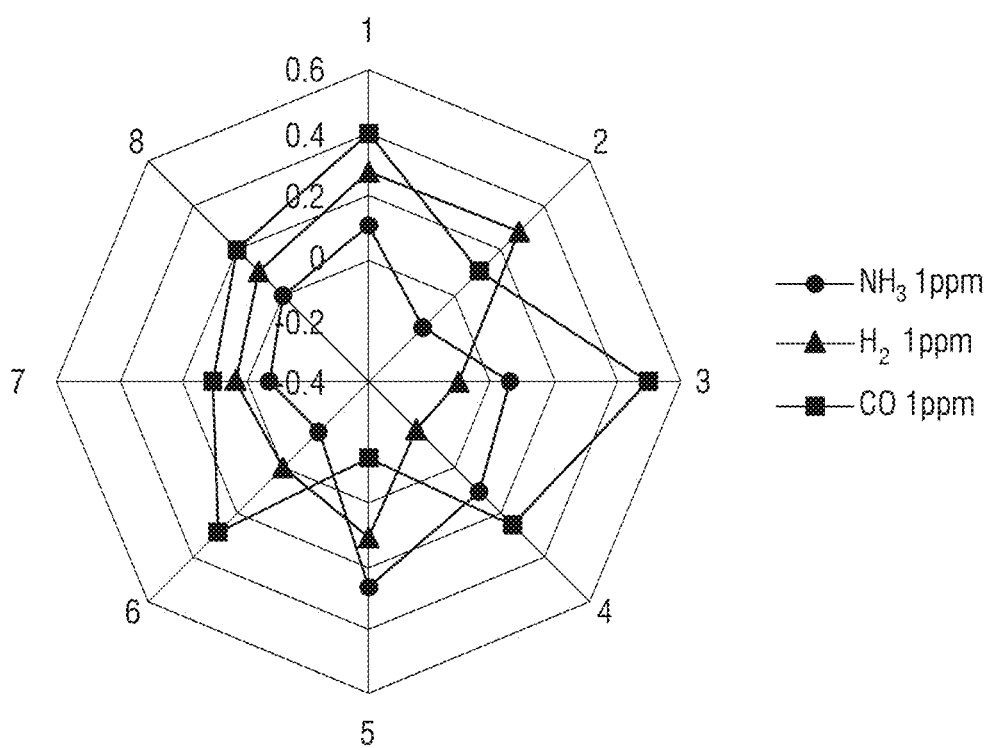
FIG. 3 is a view to compare sensing values of a plurality of semi-conductor gas sensors of different types with regard to different gases of the same concentration.

FIG. 3 is a view illustrating that different types of gases show different patterns despite having the same concentration.

Referring to FIG. 3, eight different semiconductor gas sensors may be used. Ammonia (NH3), hydrogen (H2), and carbon monoxide (CO) gases were all tested at the same 1 ppm, and the sensing value of each of eight different semiconductor gas sensors is shown in a circular diagram.

Referring to FIG. 3, the pattern of sensing values by eight semiconductor gas sensors may be different depending on the gas type despite the same concentration because the gas types are different. Therefore, the gas type may be identified based on the sensing value pattern by using a plurality of different gas sensors.

Figure 4:
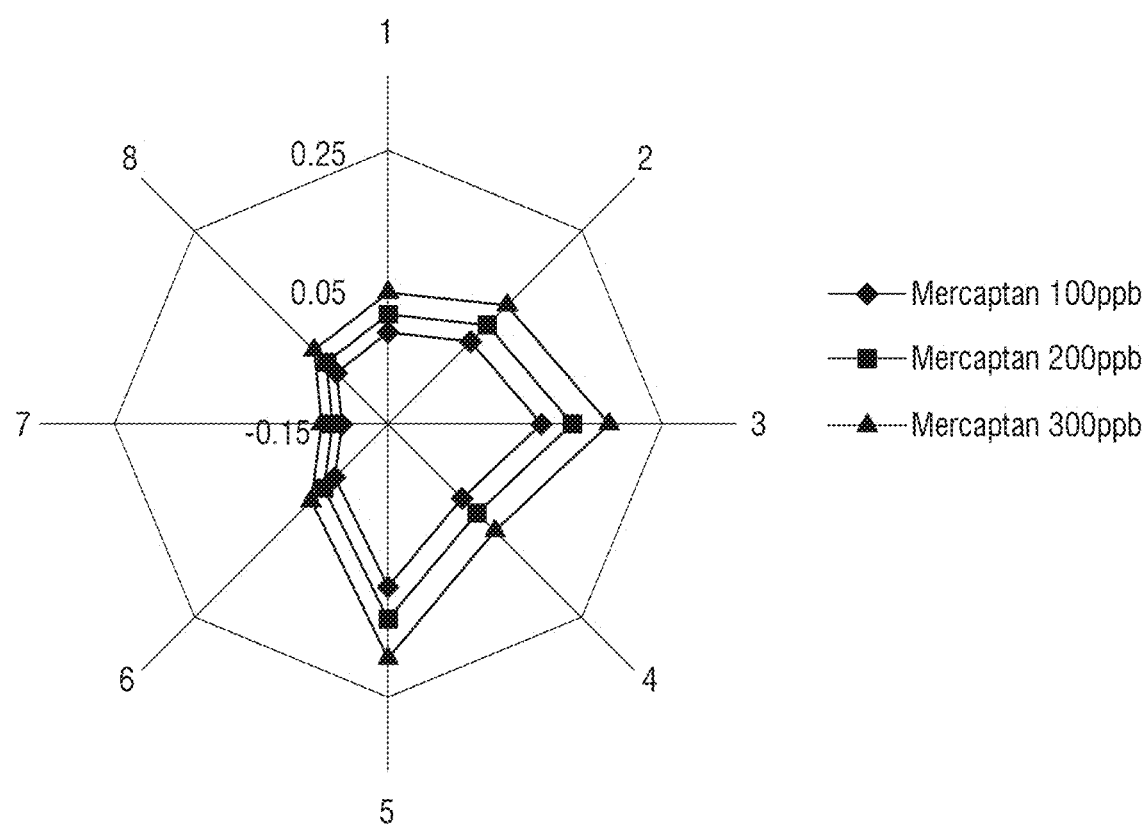
FIG. 4 is a view to compare sensing values of a plurality of semi-conductor gas sensors of different types with regard to the same gas of different concentrations.

FIG. 4 is a view illustrating a result of an experiment with the same type gas of different concentrations.

FIG. 4 shows the sensing values output from eight different semiconductor gas sensors when Mercaptan is at 100 ppb, 200 ppb and 300 ppb.

Referring to FIG. 4, if the gas type is the same, the pattern shape may be maintained even if the concentration is different. Therefore, if the basic pattern of specific gas is identified, the type of gas could be identified even if the gas is in a different concentration.

The processor 120 may control the operations of the electronic apparatus 100 overall.

According to an embodiment, the processor 120 may include at least one CPU (or DSP, MPU, etc.), RAM, ROM, and a system bus. The processor 120 may be implemented as a MICRO COMPUTER (MICOM), an application specific integrated circuit (ASIC), or the like.

The processor 120 may determine the type of gas corresponding to the sensing value output each of the plurality of gas sensors 110-1 to 110-*n*.

The electronic apparatus 100 may include a storage (not shown), and the storage may store a plurality of reference information respectively corresponding to a plurality of gases of different types.

Each of the plurality of reference information may be information on the ratio or the relationship between the plurality of sensing values output from the plurality of gas sensors 110-1 to 110-*n*, respectively corresponding to the sensing of the same gas.

To be specific, first reference information among a plurality of reference information may be information on the ratio between the plurality of sensing values respectively output from the plurality of gas sensors 110-1 to 110-*n* when a first gas in a specific concentration is sensed, second reference information may be information on the ratio between the plurality of sensing values respectively output from the plurality of gas sensors 110-1 to 110-*n* when a second gas in a specific concentration is sensed, third reference information may be information on the ratio between the plurality of sensing values respectively output from the plurality of gas sensors 110-1 to 110-*n* when a third gas in a specific concentration is sensed. Such reference information may be information on the pattern of the plurality of sensing values. The reference information may include information on the pattern of each gas as described in FIG. 2A to FIG. 2D.

The storage may store reference information corresponding to each gas that can be sensed by the plurality of gas sensors 110-1 to 110-*n*. For example, reference information corresponding to each volatile organic compound (VOC) gas such as xylene, formaldehyde (HCHO), ethylbenzene, benzene ($C_6H_6$), toluene ($C_6H_5CH_3$), acetone ($C_3H_6O$), cyclohexane, ethanol, methanol, etc. may be stored.

In addition, the storage may store information to be provided to the user when the gas is sensed as described above. Specifically, information on the source of each gas and information on the human body effect may be stored. For example, xylene may cause sick house syndrome which occurs from the material of the newly built house. Formaldehyde may give stimulation of eyes, tear, and upper airway when the concentration is 0.1 to 5, when the concentration is 10 to 20, it may give cough, headache, and accelerated heartbeat. Ethylbenzene may cause sick house syndrome. Benzene may be caused by vehicle cooling, cooking, disposable containers, gasoline (gasoline) and it may give leukemia, anemia, etc. Toluene may be used as a raw material for methyl benzene, gasoline, coating, paint, adhesive, ink, cleaning liquid, beverage bottle, polyurethane, nylon, dyes and manicure. If exposed to human body through respiratory organ or skin contact, it may cause central nervous system brain disorder, headache, depression, fatigue, loss of balance, temporary forgetfulness, and slow reaction time. When Toluene is inhaled by a pregnant woman, fetal disability may occur, and it may cause eye irritation, tear, hallucination, etc. at the concentration of 400 ppm or more, fatigue, hallucination, nausea at 600 ppm, metallic taste, eye and upper airway irritation, runny nose, drowsiness, movement disorder, dizziness at 800 ppm, even worse, it may cause cerebellar dysfunction, and cognitive decline. Also, information may be stored indicating that methanol may cause irritation on eye and respiratory organ, drowsiness, dizziness, fetal or reproductive damage, digestive system and central nervous system damage, etc.

Pollutants generated in such as fine dust, pollen, fungus, bacteria, viruses, smoke (CO) and the like as well as the above-described volatile organic compounds may also be the sensing object according to an embodiment of the disclosure. In addition, the results of living habits such as nicotine, tobacco smoke (CO), dandruff, smoke (cooking), and carbon dioxide ($CO_2$) can also be sensed, and gases generated from a disaster, and gas leakage may also be a sensing target, and information corresponding to the sensing target may be stored in the storage.

Further, the plurality of gas sensors 110-1 to 110-n may also sense components in the exhaled breath. It is possible to determine the health status of the user through analysis of the components of the exhaled breath.

For example, gases such as mentioned acetaldehyde, ethanol, acetone, IPA, 2-methyl-1, 3-butadiene, DMS, 1-propanol, 2-methyl-2-propenal, MEK, 2-Propen-1-thiol, acetic acid, ethylacetate, 3-methyl butanal, isovaleraldehyde, 1,3,5-trioxane, valeraldehyde, allyl methyl sulfide, acetoin, 3-(methylthio)-1-propene, isobutyl mercaptan, 1-(methylthio)-1-propene, isobutyric acid, 3-methyl-2-butenal, DMDS, toluene, hexanal, iso-valeric acid, 2-methyl butanoic acid, 2,4-hexadienal, 1-methoxy-2-propyl acetate, diallyl sulfide, ethylbenzene, m, p-xylene, heptanal, o-xylene, 3-Methyl-2-heptanone, 2-heptenal, benzaldehyde, alpha-pinene, 6-Methyl-5-hepten-2-one, Sabinene, Octanal, Indole, Beta-Myrcene, 1-Limonene, Disulfide, di-2-propenyl, gamma-terpinene, nonanal, diallyl tetrasulphide, decanal, nitrogen monoxide, pentane, ethane, aldehyde, carbon monoxide, carbon dioxide, ketone, alkane, hydrogen, oxygen, nitrogen dioxide, ammonia, etc. may be included in exhalation.

The reference information corresponding to the gasses may be stored in the storage.

The information on the disease corresponding to each of the gases contained in the exhaled breath may also be stored in the storage. For example, information may be stored in the storage indicating that carbon monoxide, pentane, and ethane may be associated with asthma, ethanol and aldehyde may be associated with hangover, carbon monoxide may be associated with smoking, carbon dioxide may be associated with respiration, and acetone and ketone may be associated with diabetes, and alkane may be associated with heart disease. Hydrogen may be associated with glucose malabsorption disease, carbon monoxide, oxygen, nitrogen dioxide may be associated with anesthesia, ammonia may be associated with kidney disease, and carbon monoxide may be associated with air pollution. The information may be provided to the user after transmitted to another electronic apparatus when the gas is sensed, or through a display provided on the electronic apparatus 100 itself. Meanwhile, the information may be provided from an external server instead of being stored in the electronic apparatus 100.

The processor 120 may sense reference information corresponding to a plurality of sensing values respectively output from the plurality of gas sensors 110-1 to 110-n among a plurality of reference information stored in the storage. In this case, the processor 120 may use an analysis method such as pattern recognition, principal component analysis (PCA), linear discriminant analysis (LDA), or the like, or various algorithms using a neural network.

The processor 120 may determine that the type of gas corresponding to the sensed reference information may be the type of gas sensed by the plurality of gas sensors 110-1 to 110-n.

An example of a method for sensing reference information will be described with reference to FIG. 17.

Figure 17:
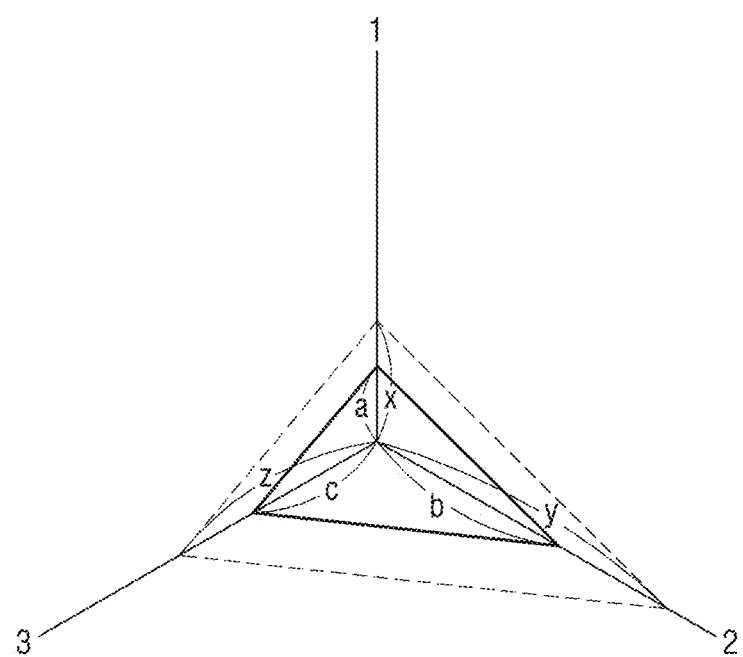
FIG. 17 is a view to explain a method for detecting gas reference information according to an embodiment.

Referring to FIG. 17, the plurality of gas sensors 110-1 to 110-n may include a first gas sensor, a second gas sensor, and a third gas sensor, and the storage of the electronic apparatus 100 may store information, for example, as the reference information of acetone indicating that the reference value of the first gas sensor is a, the reference value of the second gas senor is b, and the reference value of the third gas sensor is c. FIG. 17 is a view illustrating data for the sake of understanding, and line numbers 1, 2, and 3 may be the first, second and third gas sensors, respectively, and reference values a, b, and c may be shown on lines. The sensing values x, y and z of respective first gas sensor, second gas sensor, and third gas sensor with respect to unknown gas are shown in broken line. In order to determine which type the unknown gas is, a process of calculating a ratio between reference information may be performed.

To be specific, if 'the ratio of a:x', 'the ratio of b:y', and 'the ratio of c:z' are respectively calculated and the three ratio values are compared and determined to be similar within a predetermined error range, the unknown gas may be identified to be acetone.

For another example, if 'the ratio of a:b', and 'the ratio of x:y', 'the ratio of a:c', and 'the ratio of x:z', and 'the ratio of b:c', and 'the ratio of y:z' are respectively calculated and the three ratio values are compared and determined to be similar within a predetermined error range, the unknown gas may be identified to be acetone.

There could be two or more of reference information which is similar to the sensing value of the unknown gas within a predetermined error range. For example, as a result of calculating the ratio in the above-described manner, when reference information of benzene as well as reference information on acetone are detected as the reference information corresponding to the unknown gas, reference information having a higher similarity based on a pattern area may be determined as a final reference information. The pattern area may be an area of triangle shown in solid line and an area of a triangle shown in a dotted line referring to FIG. 17 (the case of benzene is not shown, but the area can be calculated in the same manner). If the similarity between the sensing value of the unknown gas and the reference information of benzene is higher than the similarity between the sensing value of the unknown gas and reference information of acetone considering the pattern area as well, the unknown gas may be determined to be benzene.

Meanwhile, the pre-stored reference information may be updated, or reference information corresponding to new gas may be added through machine learning.

The storage that stores the plurality of reference information may be implemented as a nonvolatile memory, a volatile memory, a flash memory, a hard disk drive (HDD), or a solid state drive (SSD). Meanwhile, the storage may be implemented not only as a storage medium in the electronic apparatus 100, but also as an external storage medium, such as a micro SD card or a USB memory.

According to another example, the plurality of reference information may be stored in an external server, the electronic apparatus 100 may transmit a plurality of sensing values output from the plurality of gas sensors 110-1 to 110-n to the external server, and the external server may detect reference information corresponding to the plurality of sensing values to provide information on gas type to the electronic apparatus 100. The external server may provide information on the gas type to a user terminal device (e.g., a smartphone) instead of the electronic apparatus 100.

It has been described that there is a single piece of reference information corresponding to a single gas, but there could be a plurality of reference information corresponding to a plurality of different concentrations of a single gas.

The processor 120 may not only determine the gas type, but also measure the concentration of the gas. To be specific, the processor 120 may measure the concentration of the gas sensed based on the magnitude of at least one of the plurality of sensing values output from the plurality of gas sensors 110-1 to 110-n.

The processor 120 may perform concentration correction based on at least two or more of sensing values output from the plurality of gas sensors 110-1 to 110-n. Therefore, the centration may be more accurately measured than the case to use only one sensing value.

According to another embodiment, the electronic apparatus 100 may further include a temperature sensor, a humidity sensor, and the like, and may correct a plurality of sensing values output from the plurality of gas sensors 110-1 to 110-n based on the sensing value at the sensor, such as a temperature sensor, a humidity sensor, a pressure sensors, etc. The temperature, humidity, and pressure may be factors affecting the state of the gas. Therefore, by identifying the state of the gas through a temperature sensor, a humidity sensor, or a pressure sensor, a more reliable sensing value of a gas sensor can be obtained.

The electronic apparatus 100 may receive peripheral information such as region information, temperature information, humidity information, pressure information, etc. of the location where the electronic apparatus 100 is disposed at the time of sensing, from the external server, and correct a sensing value based thereon. For example, when the region of the sensing value is in winter, and it is very dry and in a different environment that a normal measurement environment, a sensing value may be corrected by applying humidity correction and temperature correction. Also, it is possible to differently set a sensing value coefficient according to season, temperature, humidity, etc. and perform corrections such as multiplying the sensing value coefficient by the sensing value, or adding the sensing value coefficient to the sensing value to be reflected to the sensing value.

Such method may be generally used as a correction method that can be applied to an electronic apparatus with a sensor mounted thereon such as the temperature sensor, the humidity sensor, the pressure sensor, etc. in the above-described example embodiments other than the case of receiving the information from the external server.

Meanwhile, the storage of the electronic apparatus may include information on the characteristic of each of the plurality of gas sensors 110-1 to 110-n, for example, information on the sensor's shape, structure, etc., or information on constituent element ratio of a semiconductor layer of a semiconductor gas sensor, an open area (area where gas is transmitted), current, voltage, resistance, etc., and based thereon, the sensing value may be corrected. The electronic apparatus 100 may further include a dust sensor, etc. other than the above-described sensors, to identify overall air condition.

The electronic apparatus 100 may further include a non-dispersive infrared sensor (NDIR) for measuring the concentration of carbon dioxide ($CO_2$). However, this sensor may be pricy, which can increase the manufacturing cost of the electronic apparatus 100 and the system size.

Figure 5:
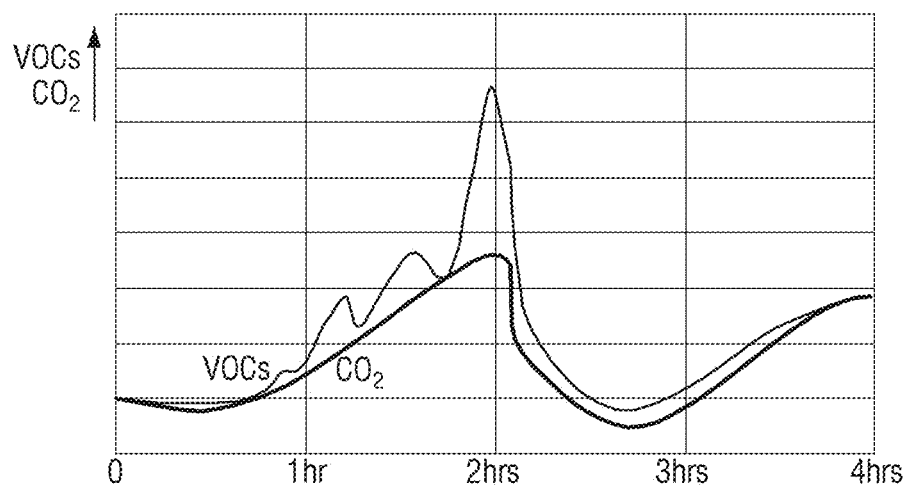
FIG. 5 is a graph showing a relationship of increasing and decreasing trend of VO and $CO_2$.

According to an embodiment, the concentration of $CO_2$ can be measured without using such a pricy sensor. The disclosure uses the technical feature that $CO_2$ similarly increases or decreases to volatile organic compound (VOC). In this regard, FIG. 5 can be referenced. Referring to FIG. 5, the higher the VOC, the higher the $CO_2$, and the lower the VOC, the lower the $CO_2$.

The processor 120, when the gas sensed by the plurality of gas sensors 110-1 to 110-n is volatile organic compounds, the concentration of the volatile organic compounds may be measured based on the magnitude of at least one of the plurality of sensing values, and the concentration of $CO_2$ may be measured based on the concentration of volatile organic compounds.

According to an embodiment, it is possible to measure the concentration of $CO_2$ without using an expensive sensor for $CO_2$, which can reduce the manufacturing cost and the system size.

The plurality of gas sensors 110-1 to 110-n and the processor 120 may be embodied as a single chip.

The electronic apparatus 100 may be embodied as an air conditioner. The air conditioner may operate in a plurality of modes, and the processor may control to operate in a mode corresponding to the type of gas determined based on the plurality of sensing values output from the plurality of gas sensors 110-1 to 110-n.

For example, the plurality of modes may include a low power mode, a normal mode, and a high power mode, and the processor 120 may control to operate in a lower power mode or a normal mode when the determined gas type is not harmful to human body.

The electronic apparatus 100 embodied as an air conditioner may further include a filter part for filtering air, and a fan for providing external air to the filter part.

The filter part may be configured to provide clean air by filtering, and may include one or more filters of various types, whereby the filter includes electrostatic precipitator, photocatalyst, HEPA, and the like.

The fan may be configured such that external air may flow into the inside of the air conditioner, pass through the filter, and be discharged to the outside.

The processor 120 may control the speed of air flowing into the inside of the air conditioner according to the determined gas type based on the plurality of sensing values output from the plurality of gas sensors 110-1 to 110-n.

For example, the processor 120 may control the rotational speed of the fan depending on the gas type determined based on the plurality of sensing values output from the plurality of gas sensors 110-1 to 110-n to maximize the clearing capacity.

The processor 120 may control the fan not to rotate or to rotate at a predetermined speed if the determined gas type is not harmful to a human body, and control the fan to rotate at a higher speed than the predetermined speed if the determined gas type is harmful to a human body, For another example, the processor 120 may control the flowing speed of air by controlling the number or type of fans to be driven depending on the gas type determined based on the plurality of sensing values output from the plurality of gas sensors 110-1 to 110-n. Conventionally, power may be consumed a lot because an air conditioner operates unnecessarily even when harmless gas (the smell of food, etc.) is generated. According to above-described examples, there in an advantage that there is no need for reducing power consumption because unnecessary operation can be avoided by identifying the gas type.

For yet another example, a plurality of modes may be a plurality of modes for filtering different types of gases. To be specific, various types of filters for various gas types may be provided in the electronic apparatus 100 which is embodied as an air conditioner, and the processor 120 may control to operate the filter corresponding to the determined gas type. In this case, the processor 120 may remove a specific noxious gas by controlling an air conditioner path so that air flows into only the filter corresponding to the determined gas type. According to an embodiment, only the filter for the object to be removed may operate, which increases the operation life time of the filter. In this regard, the disclosure is advantageous in terms of maintenance.

For yet another example, the processor 120 may control the direction of air flowing into the air conditioner depending on the gas type determined based on the plurality of sensing values output from the plurality of gas sensors 110-1 to 110-n. For example, when the determined gas type is noxious gas from the material of newly built apartment such as Formaldehyde, the processor 120 may control the direction of air flowing into the air conditioner so that the air can flow from the bottom.

Figure 6:
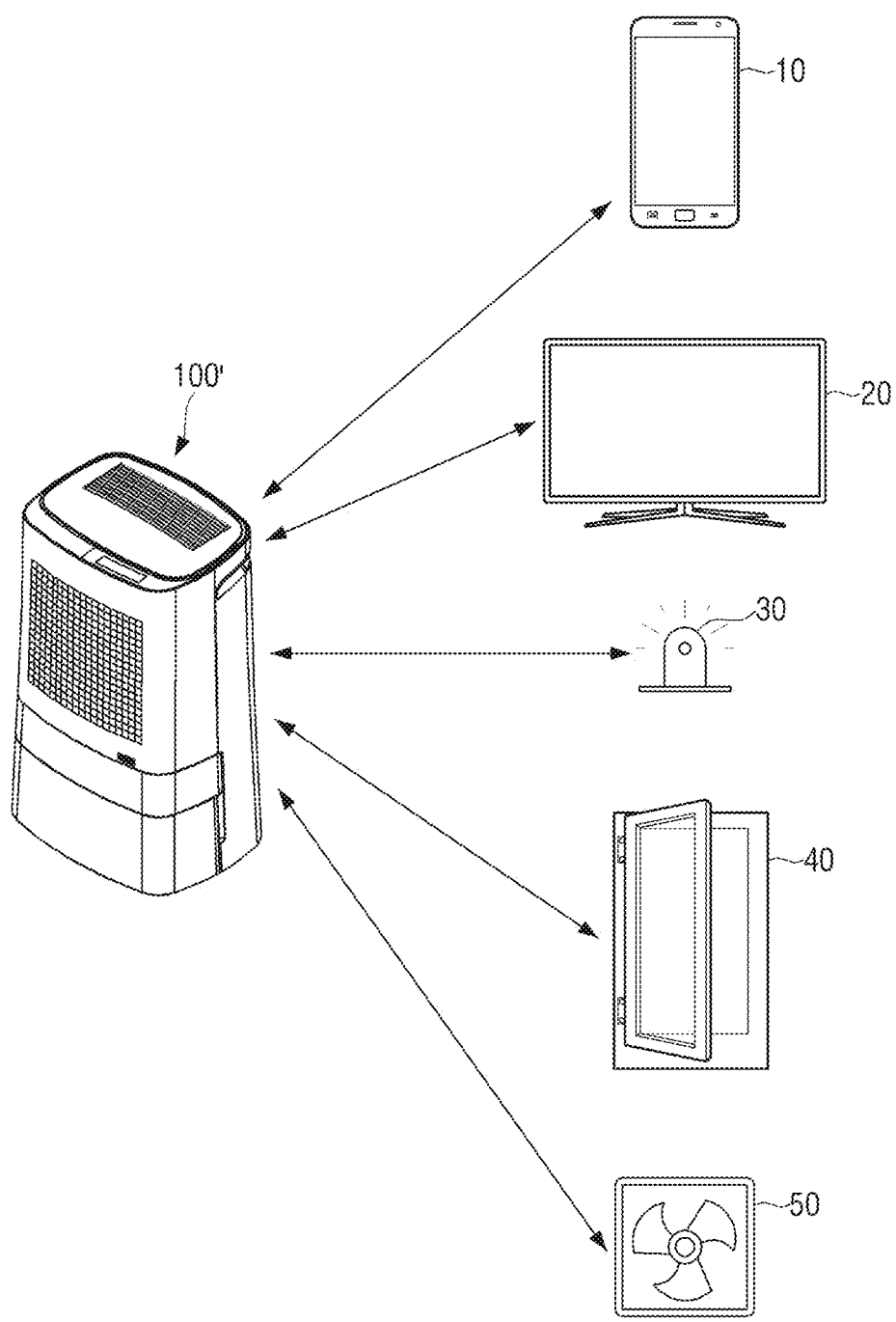
FIG. 6 is a view to explain communication between an electronic apparatus and other electronic apparatuses according to an embodiment.

FIG. 6 is a view to explain communication between an electronic apparatus 100' and other electronic apparatuses according to an embodiment.

FIG. 6 illustrates that the electronic apparatus 100' is embodied as an air conditioner, but it is not limited thereto. The electronic apparatus 100' can be embodied as a different apparatus.

The electronic apparatus 100' may further include a communicator capable of performing communication with other electronic apparatuses other than the plurality of gas sensors 110-1 to 110-n and the processor 120.

The communicator may be configured to perform communication with various external devices. The communicator may be connected to the external device via a local area network (LAN) and an Internet network, as well as wireless communication (e.g., wireless communication such as Z-wave, 4LoWPAN, RFID, LTE D2D, BLE, GPRS, Weightless, ZigBee, Edge Zigbee, ANT+, NFC, IrDA, DECT, WLAN, Bluetooth, WiFi, WiFi Direct, GSM, UMTS, LTE, WiBRO, Cellular (3/4/5G), ultrasonic waves, etc.). The communicator may include various communication chips such as a Wi-Fi chip, a Bluetooth chip, and a wireless communication chip.

The processor 120 may control the communicator to transit a control command corresponding to the gas type determined based on the plurality of sensing values output from the plurality of gas sensors 110-1 to 110-n to at least one other electronic apparatus.

For example, the processor 120 may control the communicator to transmit a control command corresponding to the determined gas type to at least one other electronic apparatus selected by display devices 10 and 20, a risk alarming device 30, a window automatic opening and closing device, 40, an air conditioner 50, or the like.

The processor 120 may transmit a control command for displaying a UI screen notifying the determined gas type to the display devices 10 and 20. For example, a UI screen including information on the description of gas and the action to be taken by a user (e.g., window opening, or fan operating) may be displayed on the display devices 10 and 20.

The processor 120 may transmit a control command for outputting alarming light or alarming sound to the danger alarming device 30 if the determined gas type is harmful to a human body.

If the determined gas type needs to be ventilated, the processor 120 may transmit a control command to open the window to the window automatic opening and closing device 40, and a control command to perform the circulating operation to the ventilation device 50.

The electronic apparatus 100' could be embodied as an apparatus for transmitting sensing values to another device, determining type and/or concentration of gas by analyzing the sensing values received another device, and performing the corresponding operation.

Meanwhile, devices capable of performing communication with the electronic apparatus 100' may vary other than those shown in FIG. 6. That is, they are not limited to the above-described examples.

Figure 7:
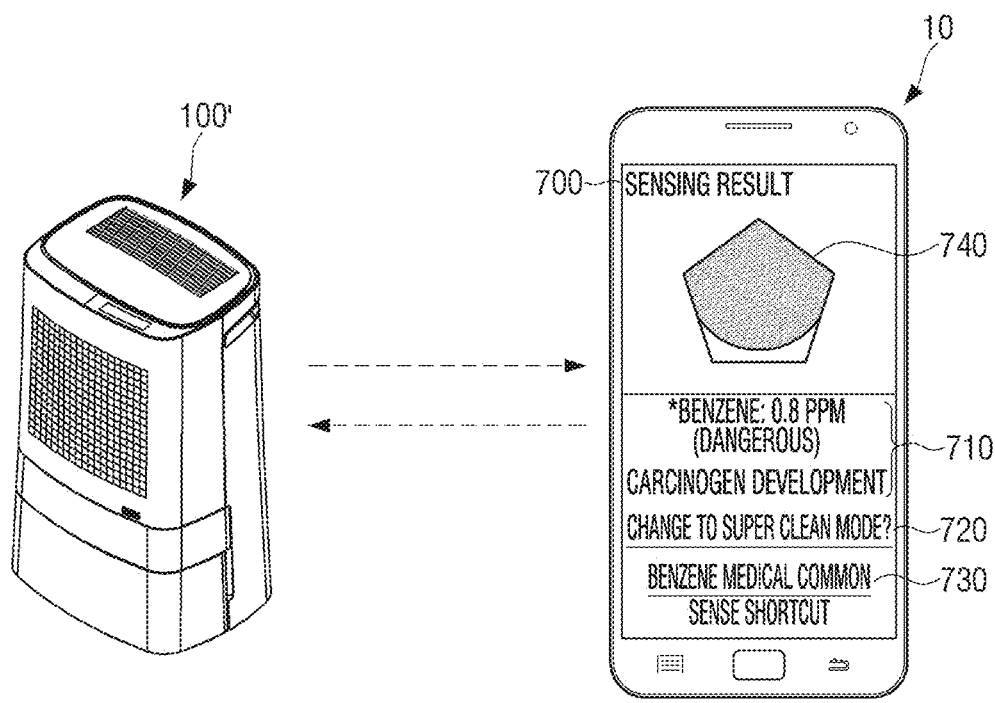
FIG. 7 is a view illustrating an example of a UI screen displayed on a display device that receives a control command from an electronic apparatus according to an embodiment.

FIG. 7 is a view illustrating an example of a UI screen displayed on a display device that receives a control command from an electronic apparatus 100' according to an embodiment.

The display device 10 may be embodied as a smartphone as shown in FIG. 7, but it is not limited thereto. The display device 10 may be embodied various devices such as a laptop computer, a PDA, a TV, etc.

The display device 10 that receives a control command from the electronic apparatus 100' may display a UI screen 700 corresponding to the control command.

The UI screen 700 may include information on the gas type determined by the electronic apparatus 100'. For example, it may include a brief description 710 of the gas, a UI element 720 to guide the air purifier control, and a UI element 730 to guide the entry into the gas details, as shown in FIG. 7. A polygon UI 740, which is a schematic representation of the characteristics of the gas being sensed, may also be displayed. The polygon UI 740 will be described in more detail with reference to FIGS. 9A to 9B.

When the UI element 720 to lead to air conditioner control is selected, the display device 10 may transmit a control command to allow to operate in a mode corresponding to the gas type to the electronic apparatus 100'. For example, when a user operation for changing a mode to a super clean mode is input to the display device 10, and the corresponding control command is transmitted to the electronic apparatus 100', the electronic apparatus 100' may operate in a super clean mode which is most excellent in filtering among a plurality of modes.

When the UI element 730 to guide to the entry to the detailed description of gas is selected, a web-page including the description of gas may be displayed on the display device 10.

When the electronic apparatus 100' includes a display, the UI may be displayed on the electronic apparatus 100'.

FIG. 6 and FIG. 7 illustrate that the electronic apparatus 100' is embodied as an air conditioner, but it could be embodied as various devices such as air conditioner, vacuum cleaner, front door, wearable device, other sensors, or the like.

For example, when the electronic apparatus 100' is embodied as an air conditioner or a vacuum cleaner, information on the contaminant degree of the filter in the air conditioner or the vacuum cleaner according to the sensing results of the plurality of gas sensors 110-1 to 110-n may be transmitted to the display device 10. By doing this, a user may receive alarming for filter change. In addition, the electronic apparatus 100' may be disposed close to the front door to transmit information on the air contaminant degree sensed near the front door to the display device 10. In this case, a user may recognize how bad she/he is contaminated by which noxious gas when got home. The electronic apparatus 100' disposed close to the front door may transmit a control command for performing an air cleaning operation to the air conditioner. It is also possible that the electronic apparatus 100' itself is embodied as a front door.

The electronic apparatus 100' may be embodied as a wearable device such as a smart watch or a patch that is worn by a user to provide information on air quality where a user stays. For example, while a user is working out, the electronic apparatus 100' may provide information on the contaminant degree of the environment where the user is exposed to.

Figure 8:
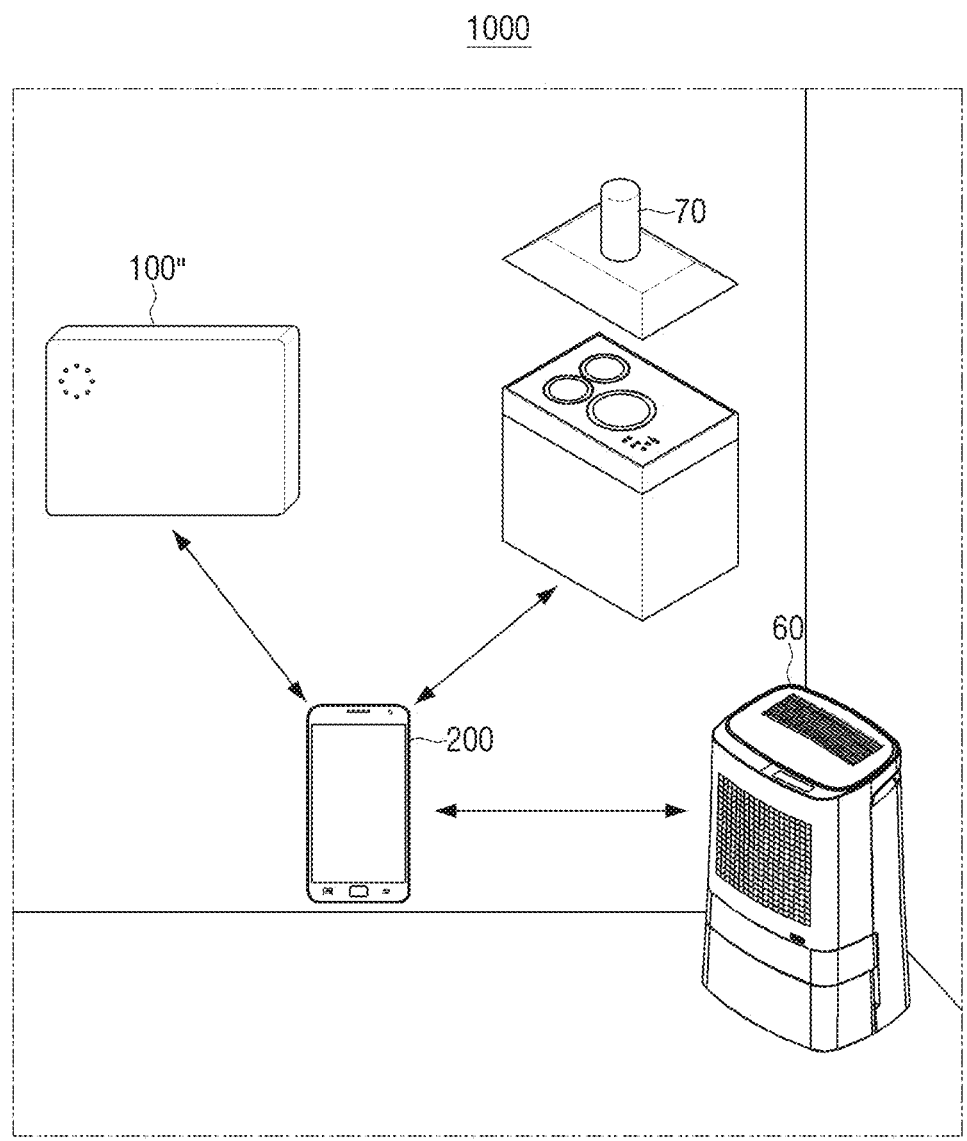
FIG. 8 is a view to explain a home network system according to an embodiment.

FIG. 8 is a view to explain a home network system according to an embodiment.

Referring to FIG. 8, a home network system 1000 may be a system in which various devices could be controlled based on a user terminal device 200.

An electronic apparatus 100" may be an apparatus including a plurality of gas sensors 110-1 to 110-n, the processor 120, and the communicator such as a gas sensing device.

The electronic apparatus 100" may transmit information on the gas type determined based on the plurality of sensing values output from the plurality of gas sensors 110-1 to 110-n to the user terminal device 200 through the communicator.

For another example, the electronic apparatus 100" may transmit the plurality of sensing values output from the plurality of gas sensors 110-1 to 110-n to the user terminal device 200, and the gas type may be determined by the user terminal device 200.

The user terminal device 200 may be a device capable of displaying various UIs based on the determined gas type, such as a smartphone.

For example, the user terminal device 200 may display the UI 700 as shown in FIG. 7. When the UI element 720 to lead to the air conditioner control is selected in the UI 700 of FIG. 7 shown in the user terminal device 200, the user terminal device 200 may transmit a control command to operate in a mode corresponding to the sensed gas type to the air conditioner 60.

The user terminal device 200 may display a UI for controlling a kitchen fan 70 based on information received from the electronic apparatus 100". The user terminal device 200 may transmit a control command for controlling a fan operation to the kitchen fan 70.

However, the description of FIG. 8 is only exemplary, and devices controlled by the user terminal device 200 based on information received from the electronic apparatus 100" may vary other than those shown in FIG. 8. For example, when gas causing an allergic disease or a lung disease is detected by the electronic apparatus 100", the user terminal device 200 may transmit a ventilation control command to the automatic window opening/closing device, a cleaning start control command to a vacuum cleaner or a robot cleaner, and a control command for air cleaning operation according to the degree of contamination to the air conditioner. Also, the user terminal device 200 may transmit a temperature control command to the air conditioner, and transmit a humidity control command to the dehumidifier.

The electronic apparatus 100" may be placed not only in the house but also outside, for example, placed outside the front door to perform an operation of sensing outdoor gas, and transmit information on the type and concentration of the sensed gas to the user terminal device 200. In this case, a user may get to know the quality of air outside without going out. In addition, the user terminal device 200 may control the air conditioner in the house to operate an air cleaning operation according to the outdoor air quality and the outdoor fine dust concentration or control the cleaner to operate.

Figure 9A:
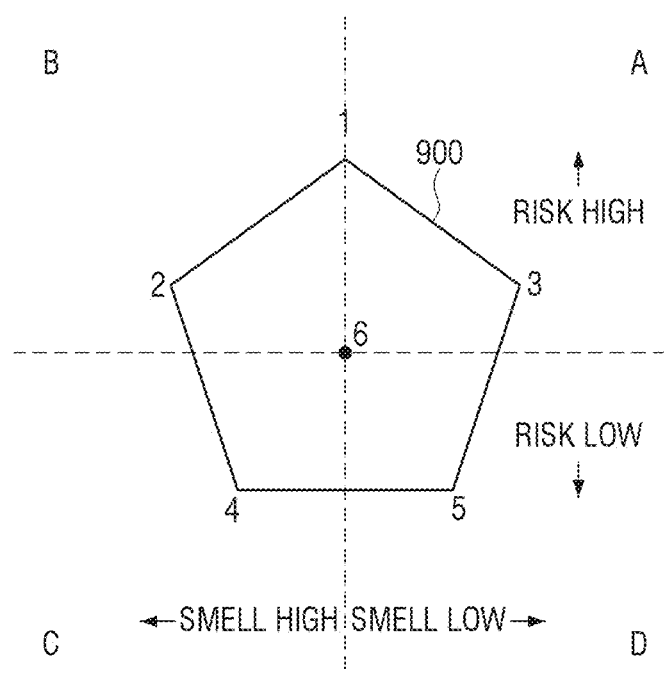
FIG. 9A to FIG. 9B are views to explain a UI for providing information on air quality sensed by an electronic apparatus according to an embodiment to a user.

FIG. 9A is a view to explain a UI for providing information on the quality of air sensed by electronic apparatuses 100, 100' and 100", and illustrates the form of UI provided according to an embodiment of the disclosure. The electronic apparatuses 100, 100' and 100" may transmit a control command for displaying the UI to the other electronic apparatus. In this case, the electronic apparatus 100, 100' and 100" may transmit only sensing values to the other electronic apparatus. The UI may be provided in the other electronic apparatus that receives sensing values, or provided by the electronic apparatus 100, 100' and 100" directly to be provided to the other electronic apparatus.

Referring to FIG. 9A, information on gas may be provided through a polygon UI 900. To be specific, the polygon UI 900 may be divided into four (4) areas A to D as shown in broken lines.

Area A may be the area for a substance less smelly toward the right and more risky upwardly, area B may be the area for a substance more smelly toward the left and more risky upwardly, area C may be the area for a substance more smelly toward the left and less risky downwardly, and area D may be the area for a substance less smelly to the right and less risky downwardly.

Figure 9B:
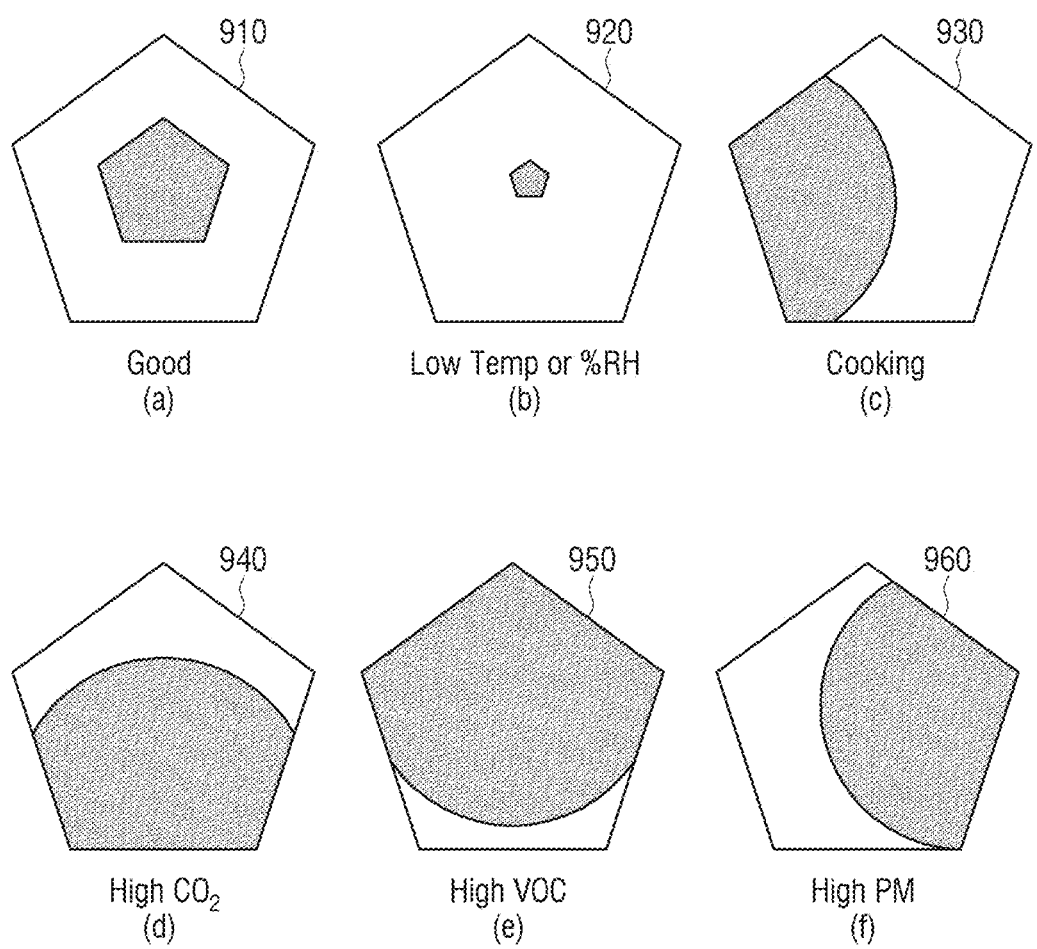

Each corner may correspond to a specific material. For example, the first vertex may be a first type of volatile organic compound, the second vertex may be a second type of volatile organic compound, the third vertex may be a particulate material (PM), the fourth vertex may be carbon monoxide, and the fifth vertex may be carbon dioxide. The first type of volatile organic compound may be a harmful substance to the human body, and the second type of volatile organic compound may be a substance which is not harmful to the human body. The center region 6 of the polygon UI 900 may be an area for temperature and humidity. Various forms of the polygon UI 900 to which this example is applied are shown in FIG. 9B. In describing FIG. 9B, FIG. 9A is also referred to.

FIG. 9B(a) is a diagram showing various examples of the display states of the first to fifth vertexes and the central area 6 described in FIG. 9 with respect to the sensing of various materials described above. Specifically, the polygon UI 910 shown in FIG. 9B (a) may include an indicator densely displayed in the center portion corresponding to the area for temperature and humidity. This indicator may indicate that the temperature and humidity are within an appropriate range, and it may indicate that the temperature and humidity correspond to "Good". Compared to this, the size of the indicator of the polygon UI 920 shown in FIG. 9B (b) may be smaller than that of FIG. 9B (a), which means that the temperature and/or humidity may be lower than the reference of "Good". In other words, as the size of the indicator increases, the temperature or the humidity may get higher, and as the size of the indicator decreases, the temperature or the humidity may get lower. According to another example embodiment, as the indicator size decreases, the temperature and the humidity may be appropriate, and if the temperature and humidity is beyond the appropriate arrange to affect to the reaction degree, the size of the indicator may be displayed to be larger, which means there is no limitation to the display of the indicator.

The polygon UI 930 shown in FIG. 9B(c) may include an indicator occupying area B and area C corresponding to the material having scent. However, the ratio of area B and area A having the highest risk is not that high. Therefore, the polygon UI 930 may indicate that there exist a material that is smelly but not risky. In addition, the indicator may imply that there exist the second volatile organic compound and the carbon monoxide which are not that harmful to the body because it leans toward the second and fourth vertexes. This would be the case of cooking food. The user may be aware of this and operate a kitchen fan.

The polygon UI 940 shown in FIG. 9B (d) may indicate an indicator occupying area C and area D which are less risky. Therefore, it may mean that air is not harmful to the human body. In addition, the indicator may imply that there exist carbon monoxide and carbon dioxide because it leans toward to the fourth and fifth vertexes. The area of the indicator in the polygon UI 940 may be relatively large, and it may mean that the concentration of carbon monoxide and carbon dioxide may be relatively high. Therefore, the user may be aware of this and open the window to circulate the air.

The polygon UI 950 shown in (e) of FIG. 9B may include an indicator occupying areas A and B corresponding to high risk areas. Since the area occupied by the indicator in the polygon UI 940 is relatively large, it can be seen that the concentration of the volatile organic compounds harmful to the human body is high. Accordingly, the user may be aware of this and open the window to ventilate the air, and more preferably, operate the air conditioner capable of filtering harmful substances.

The indicator of the polygon UI 960 shown in FIG. 9B (f) may lean forward the third convex. It may mean there exist a particle material (PM). In addition, since the area occupied by the indicator in the polygon UI 960 is relatively large, it may mean that find dust level is high. Thus, the user may be aware of this and operate an air purifier for filtering fine dust, or open the window.

The shape of the polygon UI in the above-described example and the materials assigned to the respective vertexes may be appropriately changed in accordance with the purpose. For example, the shape of the polygon UI may be a triangle, a quadrangle, or a circle instead of a pentagon as described in FIG. 9A to FIG. 9B.

The user may know comprehensive information about the air quality through such UI, and also know what action should be taken, that is, whether to operate the air purifier, operate the fan, open the window, operate the hood of kitchen, or run the heater to release the noxious gas, and the like.

According to various above-described examples, not only the concentration of gas, but also the type of gas may be distinguished. Therefore, there is an effect that the more-detailed information on gas may be provided to the user.

Figure 10A:
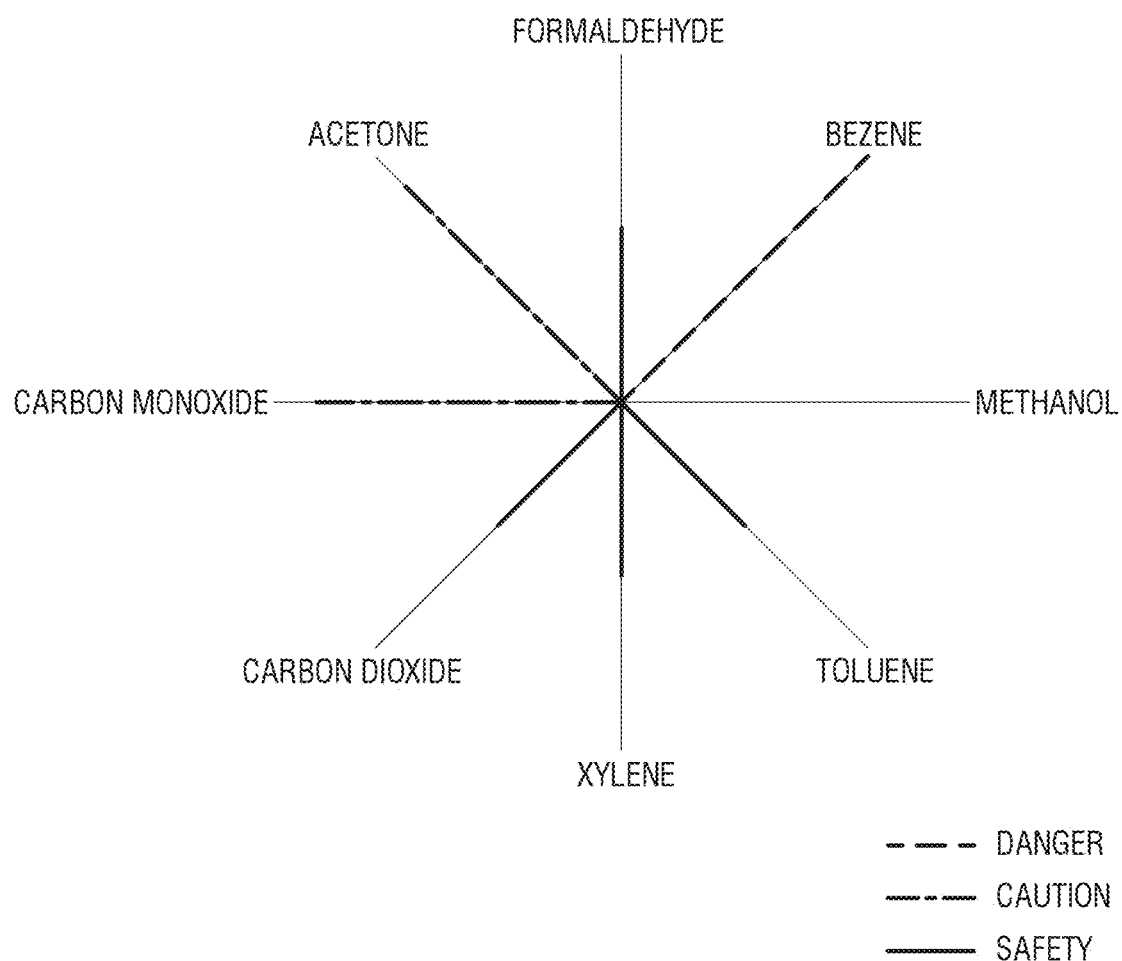
FIG. 10A to FIG. 10C are views to illustrate UIs provided by electronic apparatuses according to various embodiments.
Figure 10B:
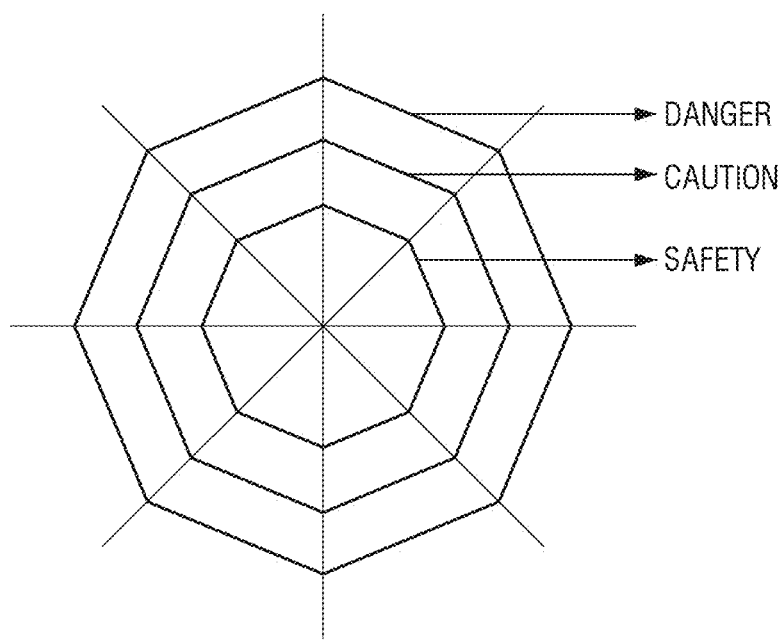
Figure 10C:
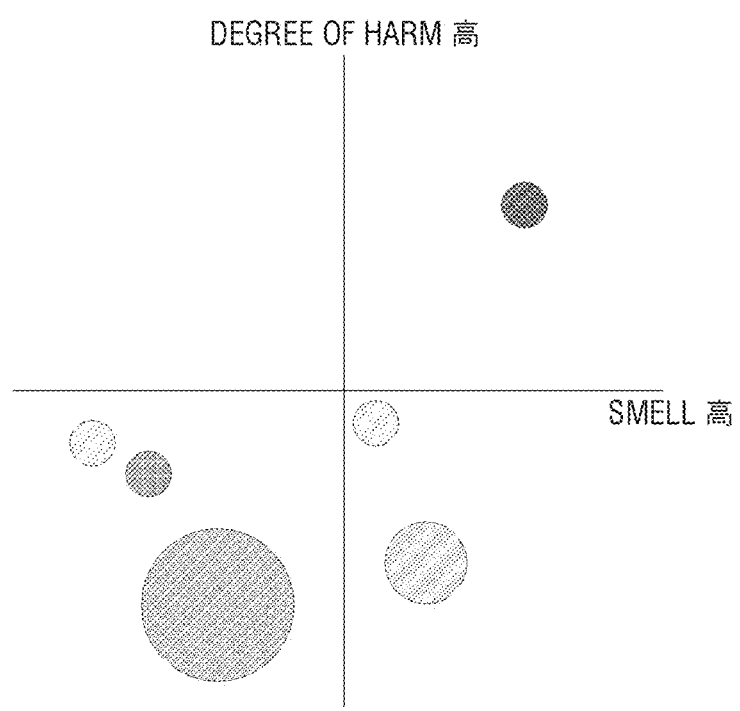

According to an embodiment, a UI for allowing to skim the distribution of actual VOC values may be provided. FIG. 10A to FIG. 10C may illustrate various examples of the UI. The electronic apparatuses 100, 100' and 100" may transmit a control command for displaying such UI to the other electronic apparatus. In this case, the electronic apparatus 100, 100' and 100" may transmit only sensing values to the other electronic apparatus. The UI may be provided from the other electronic apparatus that receives sensing values, but it is also possible for the electronic apparatus 100, 100' and 100" to directly provide the UI to be provided to the other electronic apparatus.

FIG. 10A shows an example of a UI showing a concentration distribution for a predetermined plurality of gases in a radial graph form.

Referring to FIG. 10A, lines having lengths corresponding to the concentrations of respective gases may be displayed on a radial graph. The shape or color of each line may be used to indicate either 'danger', 'attention', or 'safety'. FIG. 10B shows a UI showing a distribution of VOCs in a polygonal form, and the shape of the polygon may be changed according to the distribution of the types of detected VOCs.

In addition, higher the risk, the larger the size of the polygon. For example, based on the type and concentration of the detected VOC, any one of three polygons corresponding to the three risk levels shown in FIG. 10B may be displayed. Also, the degree of risk may be expressed by varying the thickness of the line of a polygon.

FIG. 10C is a view illustrating the UI in another form, and referring to FIG. 10C, a circular UI element corresponding to the gas may be displayed in a different color depending on the material in a quadrant, or in a different size depending on the concentration. As the degree of harmfulness of the detected gas increases, the corresponding UI element may be displayed on the top of the quadrant, and the severer the detected gas smells, the UI element may be displayed on the right side of the quadrant.

Meanwhile, in addition to the above-described embodiment, according to an embodiment of the disclosure, a UI including health information may be provided as a result of analyzing the gas generated from the user. For example, the gas in the user's exhalation may be analyzed to determine the presence or absence of diabetes, heart disease (myocardial infarction), pulmonary disease (asthma, COPD), liver disease (hepatitis), kidney disease, thyroid disease, cancer (colon cancer, pancreatic cancer, lung cancer, stomach cancer, biliary cancer, ovarian cancer, breast cancer, and prostate cancer), or information on such as allergies, immunity, fatigue/stress, alcohol (including hangover), nutritional status, and vitamin deficiency, etc., may be provided.

In addition, according to another embodiment of the disclosure, as a result of analyzing the ambient atmospheric gas, information on the possibility of sick house syndrome, information on smoking, information on fine dust, etc. may be provided. In addition, UI including information on disaster situations such as gas leaks, fires, etc. may be provided.

Figure 11:
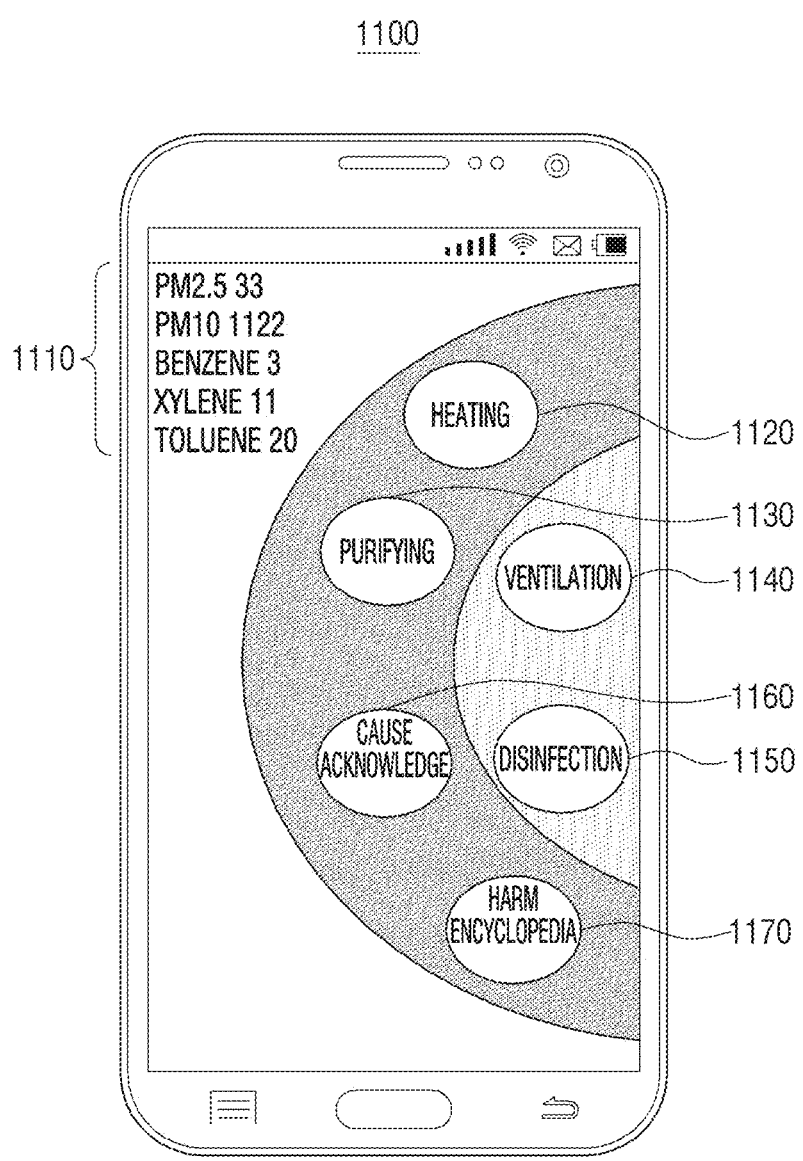
FIG. 11 and FIG. 12 are views to explain various examples of UIs according to an embodiment.
Figure 12:
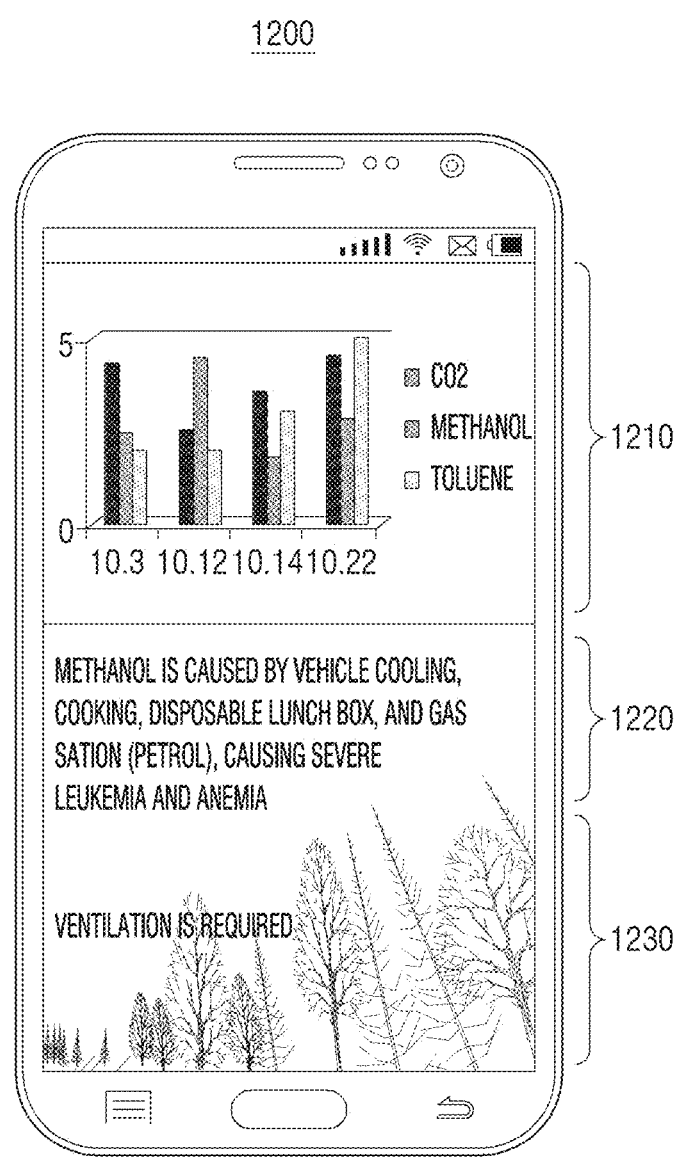

FIG. 11 and FIG. 12 are views to explain various examples of UIs to be provided according to the disclosure. The electronic apparatus 100, 100' and 100" may transmit a control command for displaying the UI to a user terminal device.

Referring to FIG. 11, a user terminal device 1100 may display information on gas. To be specific, the user terminal device 1100 may display information 1110 on gas concentration. The user terminal device 1100 may UI elements 1120, 1130, 1140, and 1150 respectively corresponding to actions to be taken by the user, and control the other electronic apparatus by selecting at least one of UI elements.

For example, when a heating UI element 1120 is selected, the user terminal 1100 may send an operation command to a boiler, and the boiler may perform the heating operation accordingly. For example, since the noxious gas discharged from the flooring material, wallpaper, etc. of the newly built house may be discharged more efficiently through heating, the noxious gas may be more effectively removed by ventilation after heating.

For another example, when a cause acknowledge element 1160 is selected, information on the cause of the sensed gas may be displayed, and when a harm UI 1170 is selected, detailed information on the sensed gas may be displayed. Such information may be stored in the storage of the user terminal device 1100, or provided from an external server.

FIG. 12 is a view to explain another UI to be provided according to the disclosure. Referring to FIG. 12, a user terminal device 1200 may display information on gas, and to be specific, history information on sensing of gas may be displayed as a UI element 1210 in a bar graph by date. In addition, information on gas 1220 and information on the action to be taken by the user 1230 may be displayed together.

Figure 13:
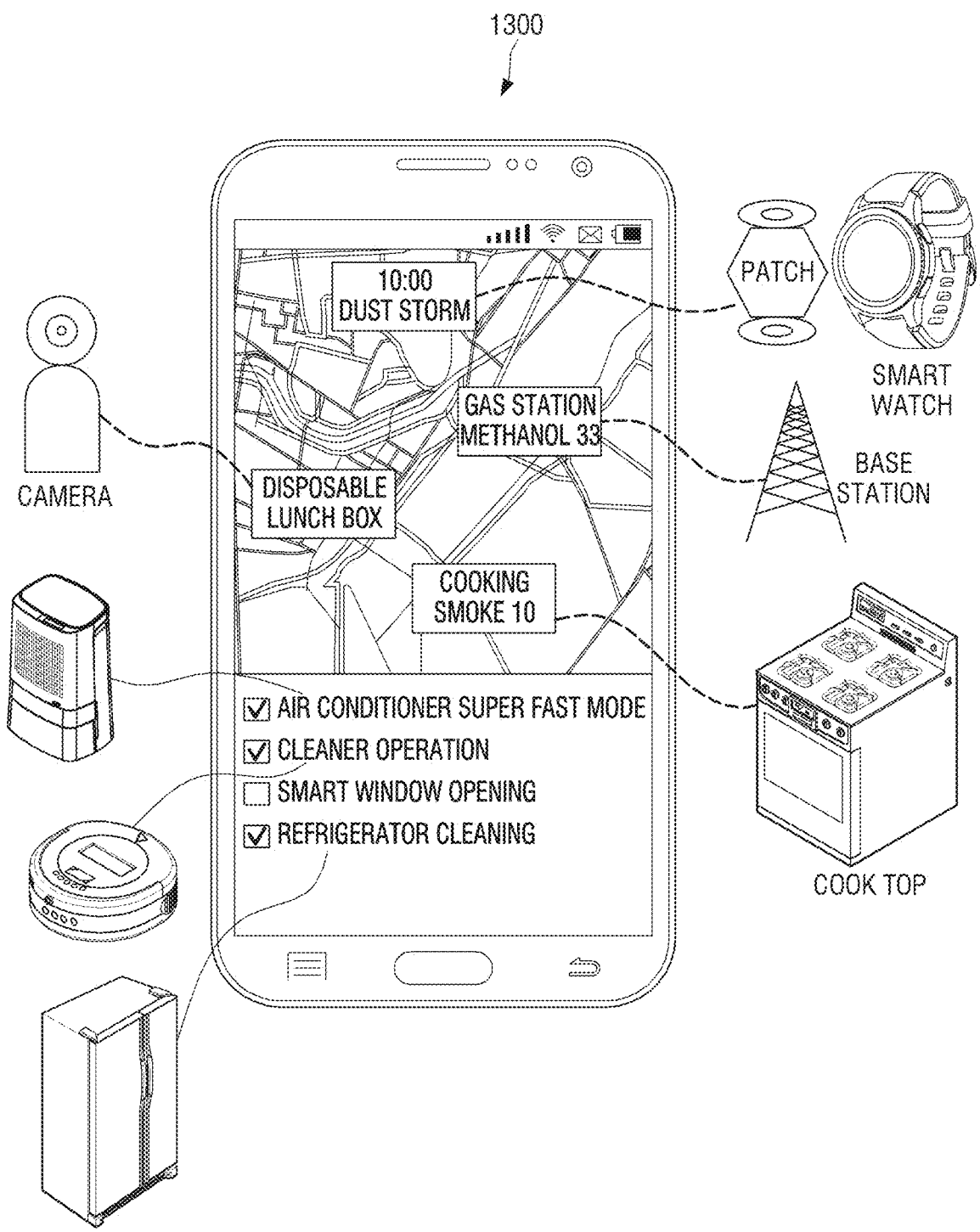
FIG. 13 is a view to explain how to control peripheral home appliances through a user terminal device according to an embodiment.

FIG. 13 is a view to explain how to control peripheral home appliances through a user terminal device based on information collected by an electronic apparatus including a plurality of gas sensors and the other electronic apparatus.

To be specific, FIG. 13 illustrates that an electronic apparatus including a plurality of gas sensors is embodied as a wearable device (patch or smart watch).

The wearable device may display information on the sensed gas through the display provided in itself, or be operable in association with the user terminal device 1300 to display the information on the user terminal device 1300.

According to an embodiment, the user terminal device 1300 may display information on the source of generation of the measured gas as well as information on the type and concentration of gas measured by the wearable device. For example, the information on the source of gas generation may be provided based on the location information of a base station connected to the wearable device. In this case, information may be displayed in the map format.

Information on the gas sensed by the wearable device may be displayed on the map along the location path where the user wearing wearable device moves.

The user terminal device 1300 may provide information on sensing object based on information collected through a peripheral device such as a camera. For example, information on the causative material (disposable lunch box) that emits the gas may be displayed through analysis of an image captured at the time of sensing the noxious gas through the wearable device.

The electronic apparatus including a plurality of gas sensors may be provided in various places. For example, the electronic apparatus may be provided near the cooking equipment (cook top) or inside the refrigerator to provide gas generated when cooking or gas generated according to the corruption of foods in the refrigerator to the user terminal device 1300.

The user terminal device 1300 may control home appliances such as an air conditioner, a robot cleaner, a refrigerator, etc. based on information on gas collected by various devices. The home appliances may be controlled manually or automatically by the user's selection through the user terminal device 1300.

Figure 14:
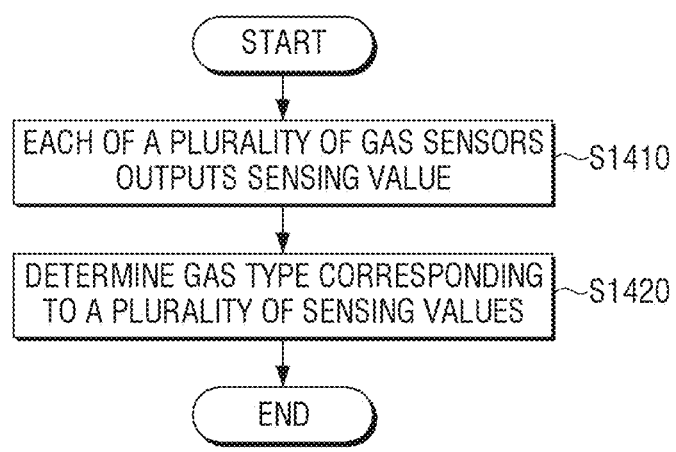
FIG. 14 is a flowchart to explain a method for controlling an electronic apparatus according to an embodiment.

FIG. 14 is a flowchart to explain a method for controlling an electronic apparatus including a plurality of gas sensors of different types according to an embodiment Referring to FIG. 14, when gas is sensed first, each of the plurality of gas sensors may output a sensing value at step S1410.

Each of the plurality of gas sensors may be a semiconductor gas sensor. The semiconductor layer included in the semiconductor gas sensor may be mainly composed of a metal oxide. For example, tin oxide ($SnO_2$) may be used. Tin oxide may be a non-stoichiometric material with oxygen vacancy, which is an n-type semiconductor in which the electrons of the oxygen vacancies move to the conduction band when heat energy is applied. When oxygen in the air is adsorbed on the surface of tin oxide, free electrons may be trapped in the oxygen gas on the surface of the particles in the O-form, and the potential barrier on the contact surface of SnO2 particles may become higher than before the adsorption of oxygen.

A reducing gas such as carbon monoxide (CO) or an inflammable gas such as LNG may desorb oxygen by reacting oxygen with adsorbed oxygen. At this time, the electrons trapped in oxygen may return to the $SnO_2$ particles, the potential barrier may become lower, and the electric conductivity may become larger. Using this principle, the concentration of the gas may be sensed by measuring the resistance change.

In addition to $SnO_2$, many materials such as ZnO, $WO_3$, $TiO_2$, and $In_2O_3$ may be used for semiconductor gas sensors. Further, a noble metal catalyst may be added to the semiconductor layer. These catalysts may increase selectivity to specific gases as well as improve sensitivity and reaction rate. In addition, oxides may be added to control the resistance of the semiconductor layer or to improve selectivity, stability, and the like.

Gag type corresponding to a plurality of sensing values respectively output from a plurality of gas sensors may be determined at step S1420.

To be specific, information on the patterns of sensing values of a plurality of gas sensors may be stored in the electronic apparatus for each gas, and the type of sensed gas may be determined by performing the pattern recognition of the output sensing value based on the stored information.

When there is no pattern corresponding to the sensing values among the stored patterns, a new pattern may be generated by combining two or more of the stored patterns, and pattern recognition may be performed with respect to the newly generated pattern. In the similar manner, two or more or types of gas in the air may be distinguished.

It is illustrated that the gas type is determined by the electronic apparatus, but the external server may perform a gas type determination operation. To be specific, the electronic apparatus may transmit sensing values output from the plurality of gas sensors to the external server. In this case, the electronic apparatus may transmit information on the plurality of gas sensors to the external server. Information on the plurality of gas sensors may include the model name of the gas sensor.

The external server may determine data base to perform pattern recognition based on information on the plurality of received gas sensors, and detect the pattern corresponding to the plurality of sensing values from the data base to determine the gas type. The information on the determined gas type may be transmitted to the electronic apparatus, or the other electronic apparatus, for example, the user terminal device.

The plurality of sensing values may be used not only for determining gas type but also the concentration of gas. To be specific, a reference table between the sensing value and the concentration may be stored in the electronic apparatus. The reference table may be provided for each of the plurality of gas sensors.

The electronic apparatus may select at least one of the plurality of measured sensing values, and determine the concentration of gas based on the reference table of the gas sensor outputting the selected sensing value. The electronic apparatus may select the greatest one of the plurality of sensing values as the sensing value for determining the concentration. This is because it is advantageous to use the sensing value output from the gas sensor having the greatest reactivity among the plurality of gas sensors for accurately measuring the concentration. Two or more of sensing values may be used for measuring the concentration.

When a plurality of gas sensors are TVOC sensors, the electronic apparatus may measure the concentration of carbon dioxide based on the measured concentration. This is based on the concentration of volatile organic compound and the similarity between the increase/decrease trends of the concentration of carbon dioxide.

The above-described electronic apparatus may be used in any field as long as it is necessary to determine the type of gas in the air. Further, according to the disclosure, not only the information on the type of the gas may be provided, but also an appropriate control operation corresponding to the gas type may be performed.

Figure 15:
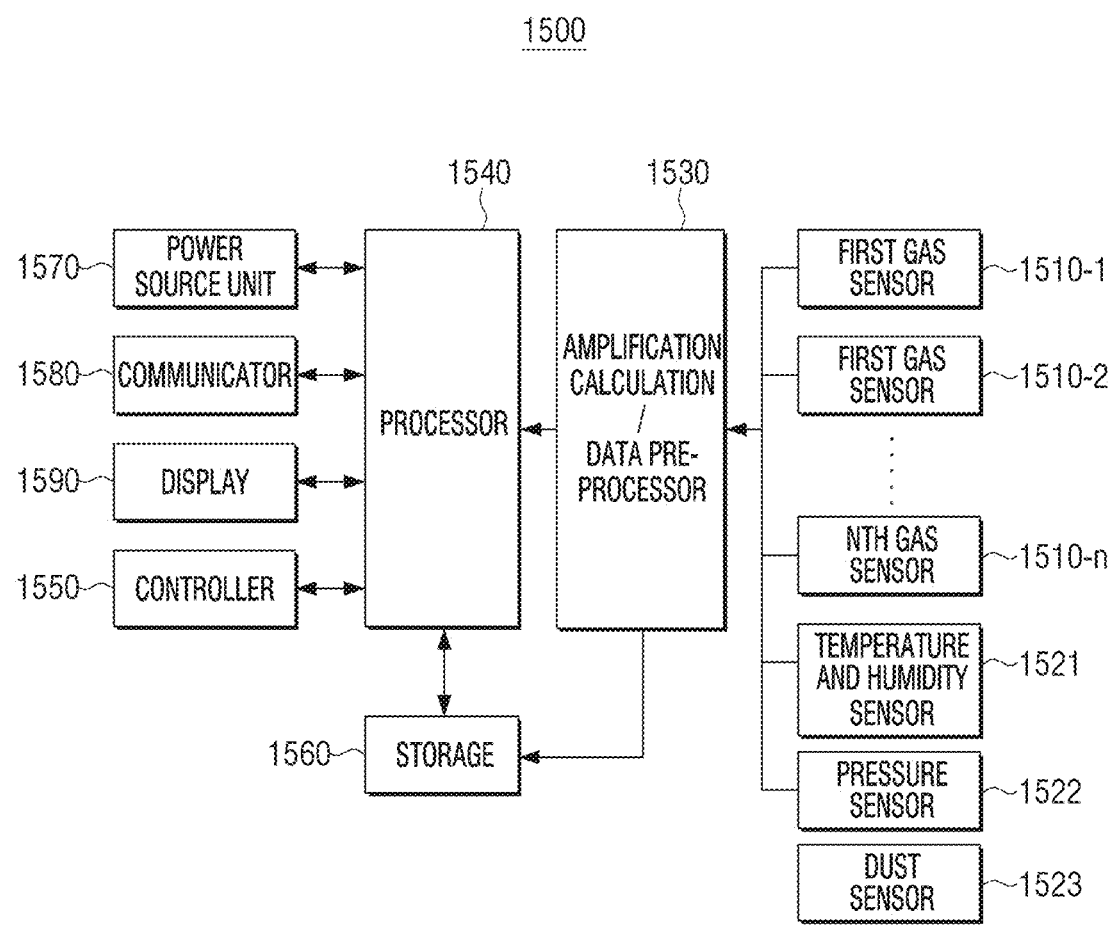
FIG. 15 is a block diagram to explain a configuration of an electronic apparatus according to another embodiment.

FIG. 15 is a block diagram to explain a configuration of an electronic apparatus 1500 according to another embodiment.

Referring to FIG. 15, an electronic apparatus 1500 may include a plurality of gas sensors 1510-1, 1510-2 and 1510-$n$, a temperature and humidity sensor 1521, a pressure sensor 1522, a dust sensor 1523, an amplification calculation/data pre-processor 1530, a processor 1540, a controller 1550, a storage 1560, a power source unit 1570, a communicator 1580, and a display 1590.

The amplification calculation/data pre-processor 1530 may perform amplification/data pre-processing with respect to the sensing values collected through the plurality of gas sensors 1510-1, 1510-2 and 1510-$n$, the temperature and humidity sensor 1521, the pressure sensor 1522, and the dust sensor 1523. The pre-processed data may be transmitted to the processor 1540, and the processor 1540 may determine the type and concentration of gas based on the sensing value collected by the plurality of gas sensors 1510-1, 1510-2 and 1510-$n$ and the information stored in the storage 1560.

The plurality of gas sensors 1510-1, 1510-2 and 1510-$n$ may be sensors capable of measuring the gas concentration through at least one of various sensing methods, for example, contact combustion method, electrochemical method (e.g., solution conduction method, constant potential electrolytic method, and diaphragm electrode method), thermal conductivity method, optical method (e.g., infrared absorption method, visible absorption method, and optical interference method), electric method (e.g., hydrogen ionization method, thermal conduction method, contact combustion method, and semiconductor method), reaction coloring method, solution conductivity method, solid electrolyte method, gas chromatography method, or the like.

The semiconductor system may use a phenomenon in which the conductivity increases when a reducing gas is adsorbed to a semiconductor of a metal oxide (N-type). In the contact combustion system, when a combustible gas is burned by a catalyst such as platinum and the temperature rises, the rise of the temperature may be detected by the increase of the electrical resistance of the platinum wire and the concentration of the reaction gas may be measured. In the electrochemical system, the concentration of gas may be measured by providing an electrode in the electrolyte (e.g., Conc-$H_2SO_4$), applying a voltage between electrodes, oxidizing gas, and measuring a current. In the thermal conductivity method, the resistance value of the platinum wire and the thermistor may be measured using the thermal conductivity determined by the surrounding gas. The optical interference method may be a method of measuring the concentration of gas using an interference pattern due to a difference in refractive index between air and a target gas. The reaction coloring method may be a method in which gas is caused to react with a liquid or solid to develop color, and the concentration of the gas is measured by measuring the coloring degree optically. The solution conductivity method may be a method in which the measurement gas is absorbed into an appropriate solution to measure the concentration of the gas by measuring the change in the conductivity of the solution. In the solid electrolyte method, when a difference in oxygen partial pressure between both sides occurs through the solid electrolyte having oxygen ion conductivity, the concentration of the gas may be measured using the electromotive force generated by the partial pressure difference.

The storage 1560 may store a library for the pattern corresponding to the sensing values of the plurality of gas sensors 1510-1, 1510-2 and 1510-$n$ for each gas type and concentration, and store the log of measurement data.

The storage 1560 may store information on a plurality of elements to determine the pattern for each of the plurality of gas sensors 1510-1, 1510-2 and 1510-$n$. To be specific, the plurality of elements to determine the pattern may include the size of the sensing value for each sensor, a threshold value for determining the reaction for each sensor, a time required for reaching a specific sensing value for each sensor, an average value of several measurements, the maximum value, the minimum value, etc.

The storage 1560 may store various types of patterns for each gas, for example, an accumulation pattern to the designated reaction time and the reaction different value pattern between sensors.

The storage 1560 may store information on the area of the pattern for determining the concentration of gas, to be specific, information on relative area, change are over time, cumulative change area, and area change value without considering time.

The processor 1540 may determine the type and the concentration of gas corresponding to the plurality of sensing values measured by the plurality of gas sensors 1510-1, 1510-2 and 1510-$n$ based on the library stored in the storage 1560.

The processor 1540 may compare data stored in the storage 1560 with the sensing values measured by the plurality of gas sensors 1510-1, 1510-2 and 1510-$n$ based on the covariance or the pattern similarity (%), and determine the type and the concentration of gas though the comparison result. In this case, the sensing values measured by the temperature and humidity sensor 1520, and the pressure senor 1522 may be used to measure the sensing values measured by the plurality of gas sensors 1510-1, 1510-2 and 1510-$n$.

The controller 1550 may generate a control command corresponding to the type and the concentration of the determined gas. In this case, the control command may be a command for controlling the electronic apparatus 1500 or a command for controlling the other electronic apparatus. For example, the controller 1550 may transmit a control command for controlling various apparatuses such as automatic window opening/closing device, robot cleaner, air purifier, air conditioner, dehumidifier, etc. based on the type and the concentration of the determined gas.

The display 1590 may include an LED that changes its color depending on the type and the concentration of the gas sensed by the plurality of gas sensors 1510-1, 1510-2 and 1510-n. In this case, the LED may change its color depending on the degree of risk of the sensed gas.

The display 1590 may include a display window of itself. The display 1590 may be embodied as, for example, Liquid Crystal Display (LCD), and in some cases, it may be embodied as a cathode ray tube (CRT), a plasma display panel (PDP), an organic light emitting diode (OLED), a transparent OLED (TOLED), and the like. In addition, the display 1590 may be embodied as a touch screen capable of sensing a user's touch operation.

Various information on the gas sensed through the display 1590 may be displayed. For example, information on the source of the sensed gas and the human influence by the gas may be displayed. If ammonia is detected, the source may be food decay. In the case of small inhalation, it may stimulate the eyes, nose, and respiratory tract, and in the case of large inhalation, the information may be displayed that people could die because of coughing, and difficulty breathing. If ozone is detected, the source may be a copy machine or household items, and information may be displayed that the cough, headache, asthma, or allergic disease may be caused by human exposure. If carbon monoxide is detected, information may be displayed that headache, reduced agility and cardiopulmonary dysfunction may be exacerbated when exposed to the human body. Such information may be stored in the storage 1560 or may be provided from the outside through the communicator 1590.

The communicator 1590 may perform communication with various types of external devices according to various types of communicator methods. The communicator 1590 may include various communication chips such as a Wi-Fi chip, a Bluetooth chip, an NFC chip, a wireless communication chip, etc. Information on the gas sensed through the communicator 1590 may be transmitted to the various devices (TV, smartphone, etc.).

Figure 16:
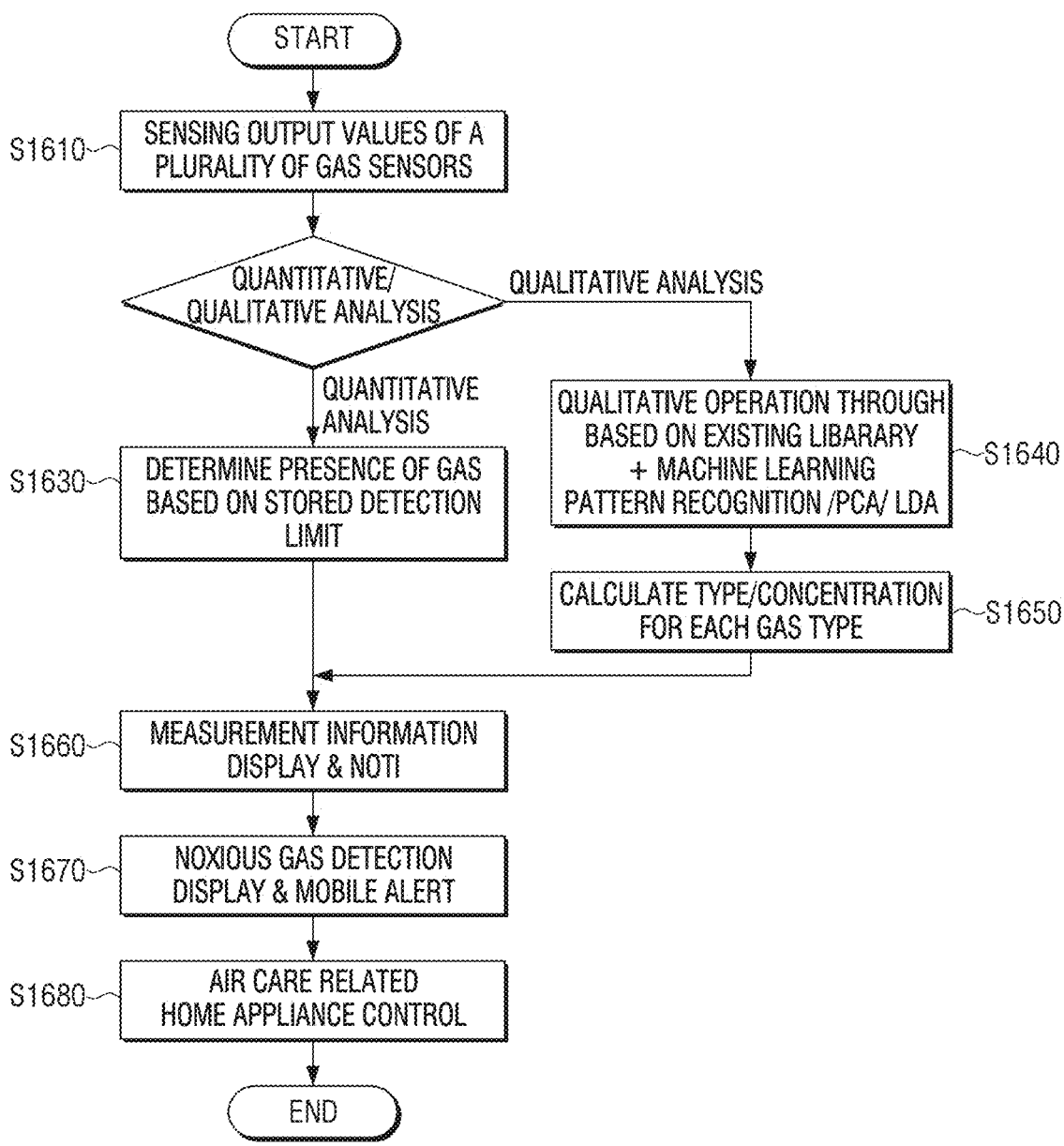
FIG. 16 is a flowchart to explain a method for controlling an electronic apparatus according to yet another embodiment.

The power source unit 1570 may supply power to an inner processor or a circuit. The power source unit 1570 may be embodied as an external battery, an adopter, etc. FIG. 16 is a flowchart to explain a method for controlling an electronic apparatus including a plurality of gas sensors according to an embodiment.

Referring to FIG. 16, output values of a plurality of gas sensors may be sensed at step S1610. In addition, quantitative analysis and qualitative analysis on the sensed values may be performed. In the qualitative analysis, whether or not the gas exists may be determined based on the previously stored detection limit at step S1630. In quantitative analysis, a quantification operation may be performed through machine learning based on a previously stored library at step S1640. In this case, specifically, a pattern recognition may be performed in which a pattern corresponding to output values of a plurality of gas sensors is compared with a previously stored library, or an analysis method such as Principal Component Analysis (PCA) or Linear Discriminant Analysis (LDA), or various algorithms using a neural network and the like may be used. The type of each gas may be determined by the above analysis, and the concentration may be calculated at step S1650.

Measurement information on the type and the concentration of gas may be transmitted to the display in the electronic apparatus or the other display device and displayed to be provided to a user at step S1660. When it is determined that the noxious gas is sensed by analysis, it may be displayed through the display provided in the electronic apparatus, or an alarming message may be transmitted to a mobile device of a user such as a smartphone, a wearable device, etc. at step S1670.

For example, in a home environment, information on fire, smoking, noxious gas, gas generated by cooking, sick house syndrome, disease, and the like may be displayed through the display of the electronic apparatus or informed by a mobile device. In an environment such as an office, a building, etc., information on the degree of pollution due to a fire or a construction material and information on the noxious gas may be displayed through the display of the electronic apparatus, or informed by the mobile device. In a word place environment such as construction side, information on the working environment (toxic gas, dust, etc.) or information environment change related to antibacterial, deodorizing, sterilizing, etc. may be displayed through the display of the electronic apparatus or informed by the mobile device. In a retail environment, information on population density ($CO_2$), noxious gas, fire, etc. may be displayed through the display of the electronic apparatus or informed by the mobile device. In addition, by sensing the information on the noxious gas in the car, for example, benzene emitted from a car air conditioner, information to guide the car ventilation may be displayed through the display of the electronic apparatus or the mobile device.

In an environment such as a hotel, information related to the degree of contamination of the furniture, bedding, air cleanliness, and the like may be displayed through the display of the electronic apparatus or informed by the mobile device. In an environment such as a school, information on the degree of bacteria, viruses, air pollution, and the like may be displayed through the display of the electronic apparatus or informed by the mobile device.

According to another example embodiment, the electronic apparatus itself may include a GPS chip, or be operable in association with a device including a GPS function such as a smart phone, the location of the electronic apparatus may be identified. In this case, when traveling unfamiliar environment like a foreign county, carrying around the electronic apparatus, information on the presence of the allergic material may be displayed through the display of the electronic apparatus, or informed by the mobile device.

The electronic apparatus may control the function of the home appliance related to the air quality care according to the type and the concentration of the gas at step S1680. For example, an electronic apparatus may be placed near a child's room or furniture to sense noxious gas, and the concentration of each type of allergen may be measured. On the basis of this, the electronic apparatus may operate the air conditioner or operate the hood, the fan, etc. so that the ventilation may be automatically performed.

In addition, the electronic apparatus may control a device such as a smart phone so that information on the type and the concentration of the measured gas may be displayed on the electronic apparatus, and accordingly, the information may be displayed on the device such as a smartphone. The device such as a smartphone may automatically control the operation of air conditioner, dehumidifier, window, robot cleaner, or the like, or display a UI screen for controlling such devices based on the information received from the electronic apparatus.

Meanwhile, the various embodiments described above can be implemented using software, hardware, or a combination thereof. According to a hardware implementation, the embodiments described in this disclosure may be implemented as application specific integrated circuits (ASICs), digital signal processors (DSPs), digital signal processing devices (DSPDs), programmable logic devices (PLDs), field programmable gate arrays (FPGAs), a processor, a controller, a micro-controller, a microprocessor, and an electrical unit for performing other functions. According to software implementation, embodiments such as the procedures and functions described herein may be implemented in separate software modules. Each of the software modules may perform one or more of the functions and operations described herein.

Meanwhile, a method for controlling an electronic apparatus according to various example embodiments of the disclosure may be stored in a non-transitory readable medium. Such non-transitory readable medium may be mounted on various devices to be used.

The non-transitory computer readable medium refers to a medium that stores data semi-permanently rather than storing data for a very short time, such as a register, a cache, and a memory, and is readable by an apparatus. Specifically, the above-described various applications or programs may be stored in a non-transitory computer readable medium such as a compact disc (CD), a digital versatile disk (DVD), a hard disk, a Blu-ray disk, a universal serial bus (USB) memory stick, a memory card, and a read only memory (ROM), and may be provided.

Although exemplary embodiments have been shown and described, it will be appreciated by those skilled in the art that changes may be made to these exemplary embodiments without departing from the principles and spirit of the present disclosure. Accordingly, the scope of the present invention is not construed as being limited to the described exemplary embodiments, but is defined by the appended claims as well as equivalents thereto.

What is claimed is:

1. An electronic apparatus, comprising:
   a plurality of different types of gas sensors configured to output sensing values based on sensing a gas;
   a plurality of filters; and
   a processor configured to:
      obtain, through the plurality of different types of gas sensors, a plurality of sensing values for the gas,
      identify a type of the gas based on comparing the plurality of sensing values and a plurality of preset reference values corresponding to the plurality of different types of gas sensors,
      control an operation of the electronic apparatus based on the identified type of the gas,
   wherein the processor is further configured to control a path of the gas so that the gas flows into a filter corresponding to the identified type of the gas among the plurality of filters.

2. The electronic apparatus as claimed in claim 1, further comprising:
   a storage configured to store a plurality of pieces of reference information respectively corresponding to the plurality of different types of gases,
   wherein the plurality of pieces of reference information is a piece of information on a ratio between the plurality of sensing values output from the plurality of different types of gas sensors corresponding to sensing a same gas.

3. The electronic apparatus as claimed in claim 1, wherein the plurality of different types of gas sensors includes a semi-conductor layer that reacts with a gas.

4. The electronic apparatus as claimed in claim 3, wherein the semi-conductor layers of the plurality of different types of gas sensors are different in at least one of constituent materials, ratios, and thicknesses of the constituent materials.

5. The electronic apparatus as claimed in claim 1, wherein the processor measures a concentration of the sensed gas based on a magnitude of at least one of the output sensing values.

6. The electronic apparatus as claimed in claim 5, wherein the processor estimates a concentration of carbon dioxide in accordance with the measured concentration based on the sensed gas being volatile organic compound (VOC).

7. The electronic apparatus as claimed in claim 1, further comprising:
   a filter configured to filter air; and
   a fan configured to provide outside air to the filter,
   wherein the processor controls a rotational speed of the fan according to the identified type of the gas.

8. The electronic apparatus as claimed in claim 7, wherein the processor is further configured to:
   control the fan not to rotate, or to rotate at a predetermined speed based on the identified type of the gas not being harmful to a human body, and
   control the fan to rotate at a higher speed than the predetermined speed based on the identified type of the gas being harmful to the human body.

9. The electronic apparatus as claimed in claim 1, further comprising:
   a communicator configured to communicate with another electronic apparatus,
   wherein the processor controls the communicator to transmit a control command corresponding to the identified type of the gas to at least one of a display device, a danger alarming device, a window automatic opening and closing device, and a ventilation device.

10. The electronic apparatus as claimed in claim 9, wherein the processor controls the communicator to transmit a control command to allow a UI screen including information on the identified type of the gas to be displayed on the display device.

11. The electronic apparatus as claimed in claim 1, further comprising:
    at least one of a temperature sensor, a humidity sensor, and a dust sensor.

12. The electronic apparatus as claimed in claim 1, wherein the plurality of different types of gas sensors and the processor are embodied as a single chip.

13. A method for controlling an electronic apparatus including a plurality of different types of gas sensors, the method comprising:
    obtaining, through the plurality of different types of gas sensors, a plurality of sensing values for the gas,
    identifying a type of the gas based on comparing the plurality of sensing values and a plurality of preset reference values corresponding to the plurality of different types of gas sensors, and
    controlling an operation of the electronic apparatus based on the identified type of the gas,
    wherein the method further comprises controlling a path of the gas so that the gas flows into a filter corresponding to the identified type of the gas among the plurality of filters.

14. The method as claimed in claim 13, further comprises: storing a plurality of pieces of reference information respectively corresponding to the plurality of different types of gases,
    wherein the plurality of pieces of reference information is a piece of information on a ratio between the plurality of sensing values output from the plurality of different types of gas sensors corresponding to sensing a same gas.

15. The method claimed in claim 13, further comprising:
measuring a concentration of the sensed gas based on a magnitude of at least one of the output sensing values.

* * * * *